(12) United States Patent
Mandala et al.

(10) Patent No.: US 7,611,851 B2
(45) Date of Patent: Nov. 3, 2009

(54) *CANIS* SPHINGOSINE 1-PHOSPHATE RECEPTOR ISOFORM 1

(75) Inventors: Suzanne M. Mandala, Scotch Plains, NJ (US); Cheryl Meyers, Sellersville, PA (US); Gan-Ju Maria Shei, Plainsboro, NJ (US)

(73) Assignee: Merck & Co., Inc., Rahway, NJ (US)

( * ) Notice: Subject to any disclaimer, the term of this patent is extended or adjusted under 35 U.S.C. 154(b) by 400 days.

(21) Appl. No.: 11/658,345

(22) PCT Filed: Jul. 22, 2005

(86) PCT No.: PCT/US2005/026059

§ 371 (c)(1), (2), (4) Date: Jan. 24, 2007

(87) PCT Pub. No.: WO2006/014802

PCT Pub. Date: Feb. 9, 2006

(65) Prior Publication Data

US 2009/0176263 A1 Jul. 9, 2009

Related U.S. Application Data

(60) Provisional application No. 60/591,333, filed on Jul. 27, 2004.

(51) Int. Cl.
*C07H 21/04* (2006.01)
*C07K 14/47* (2006.01)
*C12Q 1/02* (2006.01)

(52) U.S. Cl. .................. 435/7.2; 536/23.5; 530/350; 435/455

(58) Field of Classification Search .............. None
See application file for complete search history.

(56) References Cited

U.S. PATENT DOCUMENTS 6,423,508 B1 7/2002 Bergsma et al.
2002/0155512 A1 10/2002 Liao et al.

FOREIGN PATENT DOCUMENTS

WO WO 01/68922 A1 9/2001
WO WO 03/021220 A2 3/2003
WO WO 03/062252 A1 7/2003

OTHER PUBLICATIONS

Baumruker T et al. FTY720, an immunomodulatory sphingolipid mimetic: translation of a novel mechanism into clinical benefit in multiple sclerosis. Expert Opin. Investig. Drugs, 2007; 16(3):283-289.*

Brinkman, et al., "The Immune Modulator FTY720 Targets Sphingosine 1-Phosphate Receptors", J. of Bio. Chem., vol. 277, No. 24, pp. 21453-21457, 2002.

Chen, et al., "A Colorimetric Assay for Measuring Activation of Gs- and Gq-Coupled Signaling Pathways", Analytical Biochemistry, vol. 226, pp. 349-354, 1995.

Coward, et al., "Chimeric G Proteins Allow a High-Throughput Signaling Assay of Gi-Coupled Receptors", Annal. Biochem., vol. 270, pp. 242-249, 1999.

Forrest, et al., "Immune Cell Regulation and Cardiovascular Effects of Sphingosine 1-Phosphate Receptor Agonists in Rodents Are Mediated via Distinct Receptor Subtypes", JPET, vol. 309, No. 2, pp. 758-768, 2004.

Fukushima, et al., "Lysophospholipid Receptors," Annu. Rev. Pharmacol. Toxicol., vol. 41, pp. 507-534, 2001.

Golla, et al., "A Homogenous Enzyme Fragment Complementation Cyclic AMP Screen for GPCR Agonists", J. of Biomol. Screening, vol. 7, No. 6, pp. 515-525, 2002.

Gopalakrishnan, et al., "A cell-based microarrayed compound screening format for identifying agonists of G-protein-coupled receptors", Analytical Biochemistry, vol. 321, pp. 192-201, 2003.

Graeler, et al., "A Lymphoid Tissue-Specific Receptor, EDG6, with Potential Immune Modulatory Functions Mediated by Extracellular Lysophospholipids," Curr. Top. Microbiol. Immunol., vol. 246, pp. 131-136, 1999.

Hla, et al., "Sphingosine 1-phosphate receptors", Prostaglandins & Other Lipid Mediators, vol. 64, pp. 135-142, 2001.

Hla, et al., "Signaling and biological actions of sphingosine 1-phosphate", Pharmacoligical Research, vol. 47, pp. 401-407, 2003.

Im, et al., "Characterization of a Novel Sphingosine 1-Phosphate Receptor, Edg-8", J. of Biol. Chem., vol. 275, No. 19, pp. 14281-14286, 2000.

Kazmi, et al., "Selective Reconstitution of Human D4 Dopamine Receptor Variants with G1α Subtypes", Biochemistry, vol. 39, pp. 3734-3744, 2000.

Knight, et al., "A functional assay for G-protein-coupled receptors using stably transformed insect tissue culture cell lines", Analytical Chemistry, vol. 320, pp. 88-103, 2003.

Lee, et al., "Vascular Endothelial Cell Adherens Junction Assembly and Morphogenesis Induced by Sphingosine-1-Phosphate", Cell, vol. 99, pp. 301-312, 1999.

Liu, et al., "Edg-1, the G protein-coupled receptor for sphingosine-1 phosphate, is essential for vascular maturation", J. of Clin. Invest., vol. 106, No. 8, pp. 951-961, 2000.

Mandala, et al., "Alteration of Lymphocyte Trafficking by Sphingosine-1-Phosphate Reeptor Agonists", Science, vol. 296, pp. 346-349, 2002.

(Continued)

*Primary Examiner*—Elizabeth C. Kemmerer
*Assistant Examiner*—Kimberly A. Ballard
(74) *Attorney, Agent, or Firm*—Patricia L. Chisholm; Valerie J. Camara

(57) ABSTRACT

A *Canis* sphingosine-1-phosphate (S1P) receptor isoform 1 (cS1P$_1$), the nucleic acid encoding the cS1P$_1$ receptor, and methods for using the cS1P$_1$ receptor and the nucleic acid encoding the cS1P$_1$ receptor in assays for identifying analytes which modulate activity of the cS1P$_1$ receptor.

9 Claims, 2 Drawing Sheets

OTHER PUBLICATIONS

Niedernberg, et al., "Comparative analysis of human and rat S1P5 (edg8); differential expression profiles and sensitivities to antagonists", Biochem. Pharmacol., vol. 64, pp. 1243-1250, 2002.

Ohmori, et al., "Sphingosine 1-phosphate induces contraction of coronary artery smooth muscle cells via S1P2", Cardiovascular Research, vol. 58, pp. 170-177, 2003.

Okamoto, et al., "EDG1 Is a Functional Sphingosine-1-phosphate Receptor That Is Linked via a Gi/o to Multiple Signaling Pathways, Including Phospholipase C Activation, Ca2+ Mobilization . . . ", J. of Biol., Chem., vol. 273, No. 42, pp. 27104-27110, 1998.

Pyne, et al., "Sphingosine 1-phosphate signalling in mammalian cells", Biochem. J., vol, 349, pp. 385-402, 2000.

Salomone, et al., "S1P3 receptors mediate the potent constriction of cerebral arteries by sphingosine-1-phosphate", European J. of Pharmacology, vol. 469, pp. 125-134, 2003.

Schaphorst, et al., "Role of sphingosine-1 phosphate in the enhancement of endothelial barrier integrity by platelet-released products", Am. J. Physiol. Lung Cell Mol. Physiol., vol. 285, pp. L258-267, 2003.

Spiegel, et al., "Functions of a new family of sphingosine-1-phosphate receptors", Biochimica et Biophysica Acta, vol. 1484, pp. 107-116, 2000.

Spiegel, et al., "Sphingosine-1-Phosphate: An Enigmatic Signalling Lipid", Nat. Rev. Mol. Cell. Biol., vol. 4, No. 5, pp. 397-407, 2003.

Sugimoto, et al., "Inhibitory and Stimulatory Regulation of Rac and Cell Motility by the G12/13-Rho and Gi Pathways Integrated Downstream of a Single G Protein-Coupled Sphingosine-1-Phosphate Receptor Isoform", Mol. and Cell. Biol., vol. 23, No. 5, pp. 1534-1545, 2003.

Sugiyama, et al., "Sphingosine 1-phosphate induces sinus tachycardia and coronary vasoconstriction in the canine heart", Cardiovascular Research, vol. 46, pp. 119-125, 2000.

Sugiyama, et al., "Effects of Sphingosine 1-Phosphate, a Naturally Occurring Biologically Active Lysophospholipid, on the Rat Cardiovascular System", Jpn. J. Pharmacol., vol. 82, pp. 338-342, 2000.

Van Brocklyn, et al., "Sphingosine 1-Phosphate-induced Cell Rounding and Neurite Retraction Are Mediated by the G Protein-coupled Receptor H218", J. of Biol. Chem., vol. 274, pp. 4626-4632, 1999.

van der Wal, et al., "Monitoring Agonist-induced Phospholipase C Activation in Live Cells by Fluorescence Resonance Energy Transfer", J. of Biol. Chem., vol. 276, No. 18, pp. 15337-15344, 2001.

Varnai, et al., "Visualization of Phosphoinositides That Bind Pleckstrin Homology Domains: Calcium- and Agonist-induced Dynamic Changes and Relationship to Myo-[3H]inositol-labeled Phosphoinositide Pools", J. of Cell Biol., vol. 143, No. 2, pp. 501-510, 1998.

Yatomi, et al., "Sphingosine 1-Phosphate, a Bioactive Sphingolipid Abundantly Stored in Platelets, Is a Normal constituent of human Plasma and Serum", J. Biochem., vol. 121, pp. 969-973, 1997.

* cited by examiner atggggtccaccagcgtcccgctggtcaaggccctgcgcagtcctgtctccgactacgtcaactacgata
tcatcgtccggcactataactacacgggcaagctgaacaccagcgcggacaaggagaatggcattaaaat
gagctcggtggtgttcatcctcatctgctgctttatcatcctagagaacatcttcgtcttgctgaccatt
tggaaaaccaagaagttccaccgacctatgtactatttcatcggcaacctggccctgtctgacctgttgg
cggggggtggcctacacggccaacctgctcttgtctggcgccaccacctacaagctcacccccgctcagtg
gttcctgcgggaggggagcatgttcgtggccttgtcggcctccgtgttcagcctcctggccatcgccatc
gagcgctacatcacgatgctgaagatgaaactccacaacgggagcaacagcttccgctccttcctgctca
tcagcgcctgctgggtcatctccctggtcctgggcggcctgcccatcatgggctggaactgcatcggcgc
gctggccagctgctccaccgtgctgccgctctaccacaagcactatatcctcttctgcaccaccgtcttc
acgctgctcctgctcgccatcgtcatcctgtactgcaggatctactccctggtcaggacgcggagccgcc
gcctgaccttccgcaagaacatctccaaggccagccgcagctccgagaagtcgctggccctgctcaagac
cgtcattatcgtcctgagcgtcttcatcgcctgctgggcgccgctcttcatcctgctgctgctggacgtg
ggctgcaaggtgaagacgtgcgacatcctcttcagagccgagtacttcctggtgctggccgtgctcaact
cgggcaccaaccccatcatctacaccctcaccaacaaggagatgcgccgggccttcatccggatcctgtc
ctgctgcaagtgcccggggcggggaccccgcgggcaagttcaagcggcccatcatcgccggcgtggagttc
agccgcagtaagtcggacaactcctcccacccgcagaaggacgatggggacaacccggagaccgttatgt
cctctggaaatgtcaactcttcttcctag

SEQUENCE LISTING

<160> NUMBER OF SEQ ID NOS: 17

<210> SEQ ID NO 1
<211> LENGTH: 1149
<212> TYPE: DNA
<213> ORGANISM: Canis familiaris

<400> SEQUENCE: 1

```
atggggtcca ccagcgtccc gctggtcaag gccctgcgca gtcctgtctc cgactacgtc      60
aactacgata tcatcgtccg gcactataac tacacgggca agctgaacac cagcgcggac     120
aaggagaatg gcattaaaat gagctcggtg gtgttcatcc tcatctgctg ctttatcatc     180
ctagagaaca tcttcgtctt gctgaccatt tggaaaacca agaagttcca ccgacctatg     240
tactatttca tcggcaacct ggccctgtct gacctgttgg cggggtggc ctacacggcc      300 aacctgctct tgtctggcgc caccacctac aagctcaccc ccgctcagtg gttcctgcgg     360 gagggagca tgttcgtggc cttgtcggcc tccgtgttca gcctcctggc catcgccatc      420
gagcgctaca tcacgatgct gaagatgaaa ctccacaacg ggagcaacag cttccgctcc     480
ttcctgctca tcagcgcctg ctgggtcatc tccctggtcc tgggcggcct gcccatcatg     540
ggctggaact gcatcggcgc gctggccagc tgctccaccg tgctgccgct ctaccacaag     600
cactatatcc tcttctgcac caccgtcttc acgctgctcc tgctcgccat cgtcatcctg     660
tactgcagga tctactccct ggtcaggacg cggagccgcc gcctgacctt ccgcaagaac     720
atctccaagg ccagccgcag ctccgagaag tcgctggccc tgctcaagac cgtcattatc     780
gtcctgagcg tcttcatcgc ctgctgggcg ccgctcttca tcctgctgct gctggacgtg     840
ggctgcaagg tgaagacgtg cgacatcctc ttcagagccg agtacttcct ggtgctggcc     900
gtgctcaact cgggcaccaa ccccatcatc tacaccctca ccaacaagga gatgcgccgg     960
gccttcatcc ggatcctgtc ctgctgcaag tgcccggggc gggacccccgc gggcaagttc    1020 aagcggccca tcatcgccgg cgtggagttc agccgcagta agtcggacaa ctcctcccac    1080
ccgcagaagg acgatgggga caacccggag accgttatgt cctctggaaa tgtcaactct    1140
tcttcctag                                                            1149
```

<210> SEQ ID NO 2
<211> LENGTH: 382
<212> TYPE: PRT
<213> ORGANISM: Canis familiaris

<400> SEQUENCE: 2

```
Met Gly Ser Thr Ser Val Pro Leu Val Lys Ala Leu Arg Ser Pro Val
 1               5                  10                  15

Ser Asp Tyr Val Asn Tyr Asp Ile Ile Val Arg His Tyr Asn Tyr Thr
            20                  25                  30

Gly Lys Leu Asn Thr Ser Ala Asp Lys Glu Asn Gly Ile Lys Met Ser
        35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Lys Phe His Arg Pro Met
```

```
                65                  70                  75                  80
Tyr Tyr Phe Ile Gly Asn Leu Ala Leu Ser Asp Leu Leu Ala Gly Val
                    85                  90                  95
Ala Tyr Thr Ala Asn Leu Leu Leu Ser Gly Ala Thr Thr Tyr Lys Leu
                   100                 105                 110
Thr Pro Ala Gln Trp Phe Leu Arg Glu Gly Ser Met Phe Val Ala Leu
                   115                 120                 125
Ser Ala Ser Val Phe Ser Leu Leu Ala Ile Ala Ile Glu Arg Tyr Ile
                   130                 135                 140
Thr Met Leu Lys Met Lys Leu His Asn Gly Ser Asn Ser Phe Arg Ser
145                 150                 155                 160
Phe Leu Leu Ile Ser Ala Cys Trp Val Ile Ser Leu Val Leu Gly Gly
                   165                 170                 175
Leu Pro Ile Met Gly Trp Asn Cys Ile Gly Ala Leu Ala Ser Cys Ser
                   180                 185                 190
Thr Val Leu Pro Leu Tyr His Lys His Tyr Ile Leu Phe Cys Thr Thr
                   195                 200                 205
Val Phe Thr Leu Leu Leu Ala Ile Val Ile Leu Tyr Cys Arg Ile
210                 215                 220
Tyr Ser Leu Val Arg Thr Arg Ser Arg Arg Leu Thr Phe Arg Lys Asn
225                 230                 235                 240
Ile Ser Lys Ala Ser Arg Ser Ser Glu Lys Ser Leu Ala Leu Leu Lys
                   245                 250                 255
Thr Val Ile Ile Val Leu Ser Val Phe Ile Ala Cys Trp Ala Pro Leu
                   260                 265                 270
Phe Ile Leu Leu Leu Leu Asp Val Gly Cys Lys Val Lys Thr Cys Asp
                   275                 280                 285
Ile Leu Phe Arg Ala Glu Tyr Phe Leu Val Leu Ala Val Leu Asn Ser
                   290                 295                 300
Gly Thr Asn Pro Ile Ile Tyr Thr Leu Thr Asn Lys Glu Met Arg Arg
305                 310                 315                 320
Ala Phe Ile Arg Ile Leu Ser Cys Cys Lys Cys Pro Gly Gly Asp Pro
                   325                 330                 335
Ala Gly Lys Phe Lys Arg Pro Ile Ile Ala Gly Val Glu Phe Ser Arg
                   340                 345                 350
Ser Lys Ser Asp Asn Ser Ser His Pro Gln Lys Asp Asp Gly Asp Asn
                   355                 360                 365
Pro Glu Thr Val Met Ser Ser Gly Asn Val Asn Ser Ser Ser
                   370                 375                 380

<210> SEQ ID NO 3
<211> LENGTH: 24
<212> TYPE: DNA
<213> ORGANISM: Artificial Sequence
<220> FEATURE:
<223> OTHER INFORMATION: Primer CM001

<400> SEQUENCE: 3
gcaacagctt ccgctccttc ctgc                                              24

<210> SEQ ID NO 4
<211> LENGTH: 24
<212> TYPE: DNA
<213> ORGANISM: Artificial Sequence
<220> FEATURE:
<223> OTHER INFORMATION: Primer CM001-4
```

-continued

```
<400> SEQUENCE: 4
gcaggaagga gcggaagctg ttgc                                               24

<210> SEQ ID NO 5
<211> LENGTH: 26
<212> TYPE: DNA
<213> ORGANISM: Artificial Sequence
<220> FEATURE:
<223> OTHER INFORMATION: Primer CM012

<400> SEQUENCE: 5
catcatgggc tggaactgca tcggcg                                             26

<210> SEQ ID NO 6
<211> LENGTH: 26
<212> TYPE: DNA
<213> ORGANISM: Artificial Sequence
<220> FEATURE:
<223> OTHER INFORMATION: Primer CM012-r

<400> SEQUENCE: 6
cgccgatgca gttccagccc atgatg                                             26

<210> SEQ ID NO 7
<211> LENGTH: 23
<212> TYPE: DNA
<213> ORGANISM: Artificial Sequence
<220> FEATURE:
<223> OTHER INFORMATION: Primer CM004-r

<400> SEQUENCE: 7
tcttgcggaa ggtcaggcgg cgg                                                23

<210> SEQ ID NO 8
<211> LENGTH: 23
<212> TYPE: DNA
<213> ORGANISM: Artificial Sequence
<220> FEATURE:
<223> OTHER INFORMATION: Primer CM014-r

<400> SEQUENCE: 8
caggtcagac agggccaggt tgc                                                23

<210> SEQ ID NO 9
<211> LENGTH: 22
<212> TYPE: DNA
<213> ORGANISM: Artificial Sequence
<220> FEATURE:
<223> OTHER INFORMATION: Primer CM015-r

<400> SEQUENCE: 9
gtacataggt cggtggaact tc                                                 22

<210> SEQ ID NO 10
<211> LENGTH: 24
<212> TYPE: DNA
<213> ORGANISM: Artificial Sequence
<220> FEATURE:
<223> OTHER INFORMATION: Primer CM016-r

<400> SEQUENCE: 10
gccaggttgc cgatgaaata gtac                                               24

<210> SEQ ID NO 11
<211> LENGTH: 26
```

```
<212> TYPE: DNA
<213> ORGANISM: Artificial Sequence
<220> FEATURE:
<223> OTHER INFORMATION: Primer D5p-1

<400> SEQUENCE: 11
gccctctcca gccaaggaaa arctmc                                               26

<210> SEQ ID NO 12
<211> LENGTH: 26
<212> TYPE: DNA
<213> ORGANISM: Artificial Sequence
<220> FEATURE:
<223> OTHER INFORMATION: Primer D5p-2

<400> SEQUENCE: 12
cctcgccctc tagcgttygy ctggag                                               26

<210> SEQ ID NO 13
<211> LENGTH: 22
<212> TYPE: DNA
<213> ORGANISM: Artificial Sequence
<220> FEATURE:
<223> OTHER INFORMATION: Primer D5p-3
<220> FEATURE:
<221> NAME/KEY: misc_feature
<222> LOCATION: 5
<223> OTHER INFORMATION: n = A,T,C or G

<400> SEQUENCE: 13
ctcrncctcg ccctctagcg tt                                                   22

<210> SEQ ID NO 14
<211> LENGTH: 23
<212> TYPE: DNA
<213> ORGANISM: Artificial Sequence
<220> FEATURE:
<223> OTHER INFORMATION: Primer D5p-4r

<400> SEQUENCE: 14
saactatgat atcatmgtcc ggc                                                  23

<210> SEQ ID NO 15
<211> LENGTH: 26
<212> TYPE: DNA
<213> ORGANISM: Artificial Sequence
<220> FEATURE:
<223> OTHER INFORMATION: Primer D5p-5r

<400> SEQUENCE: 15
crgtggtgtt catyctcatc tgctgc                                               26

<210> SEQ ID NO 16
<211> LENGTH: 26
<212> TYPE: DNA
<213> ORGANISM: Artificial Sequence
<220> FEATURE:
<223> OTHER INFORMATION: Primer D5p-5r

<400> SEQUENCE: 16
caagcttatg gggtccacca gcgtcc                                               26

<210> SEQ ID NO 17
<211> LENGTH: 34
<212> TYPE: DNA
<213> ORGANISM: Artificial Sequence
<220> FEATURE:
```

-continued

```
<223> OTHER INFORMATION: Primer D5r

<400> SEQUENCE: 17
ctcccccatg ggtcggcggc tttcagttct cgag                    34
```

CANIS SPHINGOSINE 1-PHOSPHATE RECEPTOR ISOFORM 1

CROSS-REFERENCE TO RELATED APPLICATIONS

This application is a 371 national stage application of PCT US2005/026059, filed Jul. 22, 2005, which claims the benefit of U.S. Provisional Application No. 60/591,333, filed Jul. 27, 2004, the contents of which are incorporated herein by reference in their entirety.

BACKGROUND OF THE INVENTION (1) Field of the Invention

The present invention relates to a *Canis* sphingosine-1-phosphate (S1P) receptor isoform 1 ($cS1P_1$), the nucleic acid encoding the $cS1P_1$ receptor, and methods for using the $cS1P_1$ receptor and the nucleic acid encoding the $cS1P_1$ receptor in assays for identifying analytes which modulate activity of the $cS1P_1$ receptor. The assays are useful for identifying analytes with immunosuppressive activities.

(2) Description of Related Art

Sphingosine-1-phosphate is a bioactive lysolipid that mediates a variety of diverse cellular functions such as cell adhesion, motility, differentiation, proliferation, and survival (Pyne and Pyne, Biochem. J. 349: 385-402 (2000); Hla, Pharmacol. Res. 47: 401-7 (2003); Spiegel and Milstien, Nat. Rev. Mol. Cell. Biol. 4(5): 397-407 (2003)). It is a metabolic product of sphingolipids which are ubiquitous phospholipids found in all eukaryotic cells. It is also an abundant blood lipid secreted by hematopoietic cells and released from activated platelets (Yatomi et al., J. Biochem. 121: 969-73 (1997)). Many of its cell signaling functions occur through activation of a family of G protein coupled receptors (GPCRs). Five sphingosine 1-phosphate (S1P) activated GPCRs have been identified, $S1P_1$, $S1P_2$, $S1P_3$, $S1P_4$, and $S1P_5$ (previously known as endothelial differentiation genes Edg1, Edg5, Edg3, Edg6, and Edg8, respectively). These S1P receptors have a widespread cellular and tissue distribution and are well conserved in human and rodent species (Spiegel and Milstien, Biochem. Biophys. Acta 1484: 107-16 (2000); Fukushima et al., Annu. Rev. Pharmacol. Toxicol. 41: 507-34 (2001); Hla, Prostaglandins Other Lipid Mediat. 64(1-4): 135-42 (2001)).

Each S1P receptor has a unique tissue expression pattern and couples to a distinct set of heterotrimeric G proteins ($G\alpha$, $G\beta$, and $G\gamma$) each of which leads to activation of an isoform-specific panel of multiple intracellular signaling pathways. Each S1P receptor is a transmembrane protein comprising a ligand binding domain, seven transmembrane domains, and a cytoplasmic domain which interacts with $G\alpha$ of the set of heterotrimeric G proteins. In the inactive state, $G\alpha$ is bound to GDP. When sphingosine-1-phosphate binds to the ligand binding domain, a signal is transduced through the S1P receptor which results in the GDP bound to $G\alpha$ to be replaced by GTP and the $G\alpha$ to dissociate from $G\beta$ and $G\gamma$ (which remain as a $G\beta G\gamma$ dimer). $G\alpha$ and the $G\beta G\gamma$ dimer activate effectors which in turn activate distinct intracellular pathways specific to the receptor and G protein. At present, five different $G\alpha$ proteins subtypes are known; they are $G_s$, $G_{i/o}$, $G_q$, $G_{12}$, and $G_{13}$. $G_s$ activates adenyl cyclase, $G_{i/o}$ inhibits adenyl cyclase, and $G_q$ activates phospholipase C beta (PLC) which cleaves phosphoinositol-4,5 bisphosphate ($PIP_2$) in the cell membrane to release second messengers diacylglycerol (DAG) and inositol-(1,4,5)-triphosphate ($IP_3$). $G_{12}$ and $G_{13}$ interact with Rho-specific guanine nucleotide exchange factors and regulate the actin cytoskeleton. The $SIP_1$ receptor is coupled primarily via $G_{i/o}$ to inhibit adenylate cyclase and stimulate mitogen-activated protein kinase (MAPK). It is also coupled to stimulate PLC via a PTX-sensitive $G_{i/o}$. The $SIP_2$ receptor is coupled via $G_{i/o}$ to Ras/MAPK like $S1P_1$ but unlike $S1P_1$, $S1P_2$ is also coupled to stimulation of PLC via a PTX-insensitive $G_q$. It is also coupled to Rho stimulation. $S1P_3$ also interacts with multiple $G_\alpha$ subtypes including $G_{i/o}$, $G_q$, and $G_{12/13}$, whereas $S1P_4$ primarily activates $G_{i/o}$ and the MAPK pathway. The $SIP_5$ receptor is coupled via $G_{i/o}$ and $G_{12}$ to inhibit adenylate cyclase in a PTX-sensitive manner but unlike $S1P_1$, it does not stimulate MAPK.

Many of the physiological functions of sphingosine 1-phosphate and its receptors have now been elucidated. The $S1P_1$ receptor is required for vascular maturation in mice (Liu et al., J. Clin. Invest. 106: 951-61 (2000)). Ligand-induced activation of $S1P_1$ and $S1P_3$ on endothelial cells has been shown to promote angiogenesis, chemotaxis, and adherens junction assembly through Rac and Rho (Lee et al., Cell 99: 301-12 (1999)). Lung endothelial barrier function is enhanced by sphingosine 1-phosphate activation of the $S1P_1$ receptor (Schaphorst et al., Am. J. Physiol. Lung Cell Mol. Physiol. 285: L258-67 (2003)) whereas endothelial cell permeability is increased by activation of the $S1P_2$ receptor (Schaphorst et al., Am. J. Physiol. Lung Cell Mol. Physiol. 285: L258-67 (2003)). S1P activation of the $S1P_2$ receptor also inhibits chemotaxis by blocking Rac activation (Sugimoto et al., Mol. Cell. Biol. 23(5): 1534-45 (2003)) and promotes neurite retraction (Van Brocklyn, et al., J. Biol. Chem. 274(8): 4626-32 (1999)). Cardiovascular effects have been measured for sphingosine I-phosphate in rats and in dog hearts (Sugiyama et al., Jpn. J. Pharmacol. 82: 338-42 (2000); Sugiyama et al., Cardiovasc. Res. 46: 119-25 (2000); Yatomi et al., J. Biochem. 121: 969-73 (1997); Forrest et al., J. Pharm. Exp. Therap. 309: 758-768 (2004)); the $S1P_2$ receptor has been implicated in contraction of coronary arteries (Ohmori et al., Cardiovasc. Res. 58: 170-7 (2003)); and, the $S1P_3$ receptor has been found to mediate vasoconstriction of cerebral arteries (Salomone et al., Eur. J. Pharmacol. 469: 125-34 (2003)) and induce bradycardia and hypertension in rodents (Forrest et al., J. Pharm. Exp. Therap. 309: 758-768 (2004)). Pharmacological agonists of the S1P receptors are immunosuppressive; they regulate leukocyte trafficking by sequestering lymphocytes in secondary lymphoid organs (Brinkmann et al., J Biol. Chem. 277: 21453-7 (2002); Mandala et al., Science 296: 346-9 (2002). While the functions of the $S1P_4$ and $S1P_5$ receptors are less well understood, the $S1P_4$ receptor has been shown to be localized to hematopoietic cells and tissues (Graeler et al., Curr. Top. Microbiol. Immunol. 246: 131-6 (1999)) and the $S1P_5$ receptor has been shown to be primarily a neuronal receptor with some expression in lymphoid tissue in rodents but with a broader, expression pattern in human tissues (Im et al., J. Biol. Chem. 275(19): 14281-6 (2000); Niedernberg et al., Biochem. Pharmacol. 64: 1243-50 (2002)).

In light of the above, there is a need for methods for identifying analytes which modulate the activity of the $S1P_1$ receptor.

BRIEF SUMMARY OF THE INVENTION

The present invention provides a *Canis* sphingosine-1-phosphate (S1P) receptor isoform 1 ($cS1P_1$), the nucleic acid encoding the $cS1P_1$ receptor, and methods for using the $cS1P_1$ receptor and the nucleic acid encoding the $cS1P_1$ receptor in assays for identifying analytes which modulate activity of the $cS1P_1$ receptor. The assays are useful for identifying analytes with immunosuppressive activities and as such can be useful for treating a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves opthalmopathy, atopic dermatitis, and asthma; and, as part of chemotherapeutic regimens for the treatment of cancers, lymphomas, and leukemias, and regimens for inhibiting tissue rejection in organ transplants.

The present invention provides an isolated nucleic acid molecule comprising a nucleotide sequence encoding a $cS1P_1$ receptor or fragment thereof, preferably a $cS1P_1$ receptor or fragment thereof, which comprises an amino acid sequence of SEQ ID NO:2. In various embodiments, the isolated nucleic acid is a DNA, an RNA, or a cDNA. In a further embodiment of the nucleic acid, the nucleotide sequence of the nucleic acid comprises a nucleotide sequence of SEQ ID NO:1.

The present invention further provides an isolated protein or fragment thereof comprising the amino acid sequence or part thereof of SEQ ID NO:2.

The present invention further provides an antibody that binds a protein comprising the amino acid sequence or part thereof of SEQ ID NO:2. In particular embodiments, the antibody is selected from the group consisting of polyclonal antibodies, monoclonal antibodies, recombinant scFv polypeptides, recombinant $V_H$ polypeptides, and variants thereof.

The present invention further provides a vector comprising a nucleic acid encoding a $cS1P_1$ receptor or fragment thereof. Preferably, the $cS1P_1$ receptor or fragment thereof comprises an amino acid sequence of SEQ ID NO:2.

The present invention further provides a gene expression cassette comprising a nucleic acid encoding a $cS1P_1$ receptor or fragment thereof. Preferably, the $cS1P_1$ receptor or fragment thereof comprises an amino acid sequence of SEQ ID NO:2. In further embodiments of the gene expression cassette, the nucleic acid encoding the $cS1P_1$ receptor is operably linked to a heterologous promoter that can either be constitutive or inducible The present invention further provides a cell comprising a nucleic acid encoding a $cS1P_1$ receptor or fragment thereof which preferably comprises an amino acid sequence as set forth of SEQ ID NO:2 wherein the nucleic acid is operably linked to a heterologous promoter which can either be constitutive or inducible. In a further embodiment of the cell, the nucleic acid is integrated into the genome of the cell.

The present invention further provides a method for producing a $cS1P_1$ receptor comprising providing a nucleic acid encoding the $cS1P_1$ receptor operably linked to a heterologous promoter; introducing the nucleic acid into a cell to produce a recombinant cell; and culturing the recombinant cell under conditions which allows expression of the $cS1P_1$ receptor encoded by the nucleic acid to produce the $cS1P_1$ receptor.

In a further embodiment of the method, the nucleic acid is integrated into the genome of the recombinant cell. In a further still embodiment of the method, the $cS1P_1$ receptor comprises the amino acid sequence of SEQ ID NO:2.

The present invention is particularly useful for identifying analytes that have immunosuppressive activity. Therefore, the present invention further provides a method for screening for analytes with an immunosuppressive activity useful for treating autoimmune and inflammatory diseases, as a component of a chemotherapeutic regimen for treating cancers, or a regimen for inhibiting tissue rejection of transplants in a mammal, which comprises in one aspect determining the activity of a $cS1P_1$ receptor in the presence of a particular concentration of the analyte or in the absence of the analyte, and determining the activity of the $cS1P_1$ receptor at a different concentration of the analyte. The screening method can be cell-based or cell-free and can comprise one or more embodiments of the functional or binding assays set forth below.

Functional assays include a method for identifying an analyte that modulates activity of a $cS1P_1$ receptor, which comprises providing a recombinant cell which produces the $cS1P_1$ receptor; incubating the recombinant cell in a medium with the analyte; and determining the activity of the $cS1P_1$ receptor wherein a change in the activity of the $cS1P_1$ receptor indicates the analyte modulates activity of the $cS1P_1$ receptor.

The activity of the $cS1P_1$ is determined by one or more means for measuring $S1P_1$ activity selected from the group consisting of measuring a change in the intracellular concentration of $Ca^{2+}$ in the presence of the analyte; measuring a change in the intracellular concentration of a metabolite selected from the group consisting of inositol triphosphate ($IP_3$) and diacylglycerol (DAG) in the presence of the analyte; measuring a change in the activity of phospholipase C beta ($PLC_\beta$) or protein kinase C (PKC) in the presence of the analyte; and measuring a change in the synthesis of cyclic AMP (cAMP) in the presence of the analyte. In assays that measure the change in the synthesis of the cAMP, $Ca^{2+}$, or other signaling molecules, an embodiment is further provided wherein measuring the change in signaling molecule is accomplished by including in the recombinant cell a gene expression cassette comprising a reporter gene which encodes an assayable product (e.g., a reporter gene encoding luciferase, β-lactamase, secreted alkaline phosphatase (SEAP), or the like) operably linked to a promoter which is responsive to the signaling molecule.

In further still embodiments of the above method, the recombinant cell further produces a chimeric protein G or a promiscuous G protein. The chimeric G protein can be selected from the group consisting of $G\alpha_{qo5}$ and $G\alpha_{q55}$ and the promiscuous G protein can be selected from the group consisting of $G\alpha_{15}$ or $G\alpha_{16}$. In a further embodiment of the method, the $cS1P_1$ comprises the amino acid sequence of SEQ ID NO:2. In a further still embodiment of the method, the $cS1P_1$ and/or the chimeric or promiscuous G protein are encoded by gene expression cassettes, which in particular aspects, are integrated into the genome of the recombinant cell. Therefore, the recombinant cell can be transiently or stably transfected with one or more gene cassettes selected from the group consisting of gene cassettes encoding the $cS1P_1$ receptor, a chimeric or promiscuous G protein, and a reporter gene expression cassette.

The present invention further provides a method for identifying an analyte that binds to a $cS1P_1$ receptor, which comprises providing a recombinant cell which produces the $cS1P_1$ receptor; incubating the recombinant cell in a medium with the analyte; and, determining the amount of the analyte bound to the recombinant cell. Analytes which have been identified to bind to the $cS1P_1$ receptor using the aforementioned assays can be further analyzed using one of the functional assays above to determine whether the analyte is an agonist or an antagonist.

In a further embodiment of the method, the $cS1P_1$ comprises the amino acid sequence of SEQ ID NO:2. In a further still aspect of the method, the $cS1P_1$ is encoded by a nucleic acid which in particular embodiments is integrated into the genome of the recombinant cell. In a further embodiment of the above method, a competition assay is provided wherein the recombinant cell is incubated in a medium comprising the analyte and labeled S1P and the amount of analyte bound to the $cS1P_1$ receptor on the surface of the recombinant cell is determined by measuring the amount of labeled S1P bound to the recombinant cell. A decrease in the amount of label bound to the recombinant cell indicates that the analyte is a competitor of the labeled S1P for binding to the $cS1P_1$ receptor. In a further still embodiment, the analyte is labeled and the amount of analyte bound to the recombinant cell is determined either alone or in competition with differing concentrations of unlabeled S1P.

The present invention further provides a method for determining whether an analyte is a $cS1P_1$ receptor agonist or antagonist, which comprises providing a membrane which has the $cS1P_1$ receptor integrated therein and a G protein heterotrimer associated therewith; incubating the membrane in the presence of the analyte and labeled GTP for a time sufficient for the labeled GTP to be associated with the membrane when an agonist is present; and separating the membrane from unbound labeled GTP and determining the amount of labeled GTP associated with the membrane wherein an increase in the labeled GTP associated with the membrane indicates that the analyte is an agonist, a decrease in the labeled GTP associated with the membrane indicates that the analyte is an inverse agonist, and a decrease in the labeled GTP associated with the membrane in the presence of S1P or known agonist indicates that the analyte is an antagonist.

In a further embodiment of the method, the $cS1P_1$ comprises the amino acid sequence of SEQ ID NO:2. In a further still aspect of the method, the membrane is provided by a recombinant cell comprising a nucleic acid encoding the $cS1P_1$. In a further still embodiment of the method, the medium comprises the analyte and a labeled sphingiosine-1-phosphate (SIP). In further still embodiment, the labeled GTP is labeled GTPγS. In particular aspects of the above, the analyte is labeled.

DEFINITIONS

The term "$cS1P_1$ receptor" means that the $S1P_1$ receptor is of *Canis* (dog) origin, either isolated from dog tissue, produced from a nucleic acid obtained from the dog by recombinant means, produced from a nucleic acid synthesized in vitro but which encodes the $cS1P_1$ receptor, or synthesized in vitro. The term further includes biologically active fragments or portions of the $cS1P_1$ receptor, including fusion or chimeric proteins.

The term "$S1P_1$ receptor" means that the $S1P_1$ receptor is not of dog origin. The $S1P_1$ receptor can be from another organism, for example, a mammal such as rat and mouse, or a human. The $S1P_1$ receptor can either be isolated from tissue of the organism, produced from a nucleic acid obtained from the organism by recombinant means, produced from a nucleic acid synthesized in vitro but which encodes the $S1P_1$ receptor, or synthesized in vitro. The term further includes biologically active fragments or portions of the $S1P_1$ receptor, including fusion or chimeric proteins.

The term "promoter" refers to a recognition site on a DNA strand to which RNA polymerase binds. The promoter forms an initiation complex with RNA polymerase to initiate and drive transcriptional activity of a nucleic acid sequence located downstream from the promoter. The promoter can be modified by including activating sequences termed "enhancers" or inhibiting sequences termed "silencers" within the promoter. The term further includes both promoters which are inducible and promoters which are constitutive.

The term "gene expression cassette" refers to a nucleotide or gene sequence that is to be expressed from a vector, for example, the nucleotide or gene sequence encoding the $cS1P_1$ receptor, a reporter gene, or a chimeric or promiscuous G protein. In general, a cassette comprises a gene sequence inserted into a vector which in some embodiments provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector or included in the nucleotide sequence include, but are not limited to, promoters, enhancers, transcription termination sequences, splice acceptor and donor sequences, introns, ribosome binding sequences, and poly(A) addition sequences.

The term "vector" refers to a means by which DNA fragments can be introduced into a host organism or host tissue. There are various types of vectors including plasmid, virus (including adenovirus, herpesvirus, and the like), bacteriophage, and cosmid.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

The term "agonist" refers to an agent that mimics or upregulates (for example, potentiates or supplements) $cS1P_1$ receptor bioactivity (and, therefore, human $S1P_1$ activity). An agonist can also be an analyte that upregulates expression of the $cS1P_1$ receptor. Agonists include proteins, nucleic acids, carbohydrates, small molecules, or any other molecule which can activate the $cS1P_1$.

The term "antagonist" refers to an analyte that inhibits, decreases, or suppresses a bioactivity of $cS1P_1$ receptor (and, therefore, human $S1P_1$ receptor). An antagonist can be an analyte that decreases signaling from the $cS1P_1$ receptor, for example, an analyte that is capable of binding to the $cS1P_1$ or human $S1P_1$ receptor. A preferred antagonist inhibits or suppresses the interaction between $cS1P_1$ receptor (and, therefore, human $S1P_1$ receptor) and its ligand. Alternatively, an antagonist can be a compound that downregulates expression of the $cS1P_1$ receptor gene. Antagonists include proteins, nucleic acids, carbohydrates, antibodies, small molecules, or any other molecule which can decrease the activity of the $S1P_1$ receptor.

Both agonists and antagonists modulate activity of the $cS1P_1$ receptor.

As used herein, the term "modulate", refers to any change in the activity of the $cS1P_1$ receptor effected by the analyte. For example, modulation may cause an increase or a decrease in protein activity, binding characteristics, or any other biological, functional, or immunological properties of the $S1P_1$ receptor. A modulator of $S1P_1$ activity can be an agonist or an antagonist.

A "disorder" is any condition that would benefit from treatment with analytes identified by the methods described herein. This includes chronic and acute disorders or diseases including those pathological conditions which predispose the mammal to the disorder in question.

The term "mammalian" refers to any mammal, including a human being.

The term "treatment" refers to both therapeutic treatment and prophylactic or preventative measures. Those in need of treatment include those already with the disorder as well as those prone to have the disorder or those in which the disorder is to be prevented.

The term "analyte" refers to compound, composition, drug, molecule, peptide, protein, carbohydrate, nucleic acid, peptidomimetics, and the like, which interact with directly or indirectly with the cS1P$_1$ receptor.

BRIEF DESCRIPTION OF THE DRAWINGS

FIG. 1 shows the nucleotide sequence encoding the cS1P$_1$ receptor (SEQ ID NO:1).

FIG. 2 shows the amino acid sequence comprising the cS1P$_1$ receptor (SEQ ID NO:2).

DETAILED DESCRIPTION OF THE INVENTION

Figure 3:
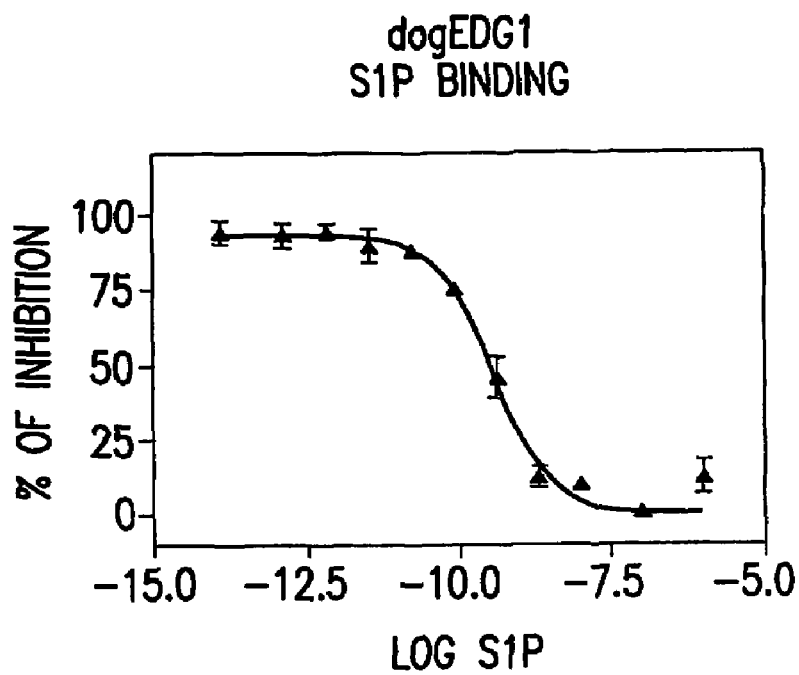
FIG. 3 shows the results of an S1P ligand binding assay using the cS1P$_1$ receptor.

The present invention provides nucleic acid molecules that encode the *Canis* (dog) sphingosine-1-phosphate isoform 1 receptor (cS1P$_1$ or cEdg1 receptor) and provides methods for using the nucleic acid molecules and the cS1P$_1$ receptor produced therefrom in assays for identifying analytes (molecules, compounds, drugs, or compositions) that modulate the activity of the cS1P$_1$ receptor by interacting with or binding the cS1P$_1$ receptor or modulating the molecular or functional interaction between the cS1P$_1$ receptor and its ligand sphingosine-1-phosphate (S1P). Modulators of cS1P$_1$ activity can be agonists, inverse agonists or antagonists. Many S1P$_1$ receptor agonists have immunosuppressive activities by producing lymphocyte sequestration in secondary lymphoid tissues (WO2003062252 to Bugianesi et al.). Thus, the assays disclosed herein are useful for identifying analytes with immunosuppressive activities. Analytes with immunosuppressive activity have been shown to be useful in treating a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmnune myositis, Wegener's granulomatosis, ichthyosis, Graves opthalmopathy, atopic dermatitis, and asthma (WO2003062252 to Bugianesi et al.). Analytes with immunosuppressive activity have also proved useful as part of chemotherapeutic regimens for the treatment of cancers, lymphomas, and leukemias, and regimens for inhibiting tissue rejection in organ transplants (WO2003062252 to Bugianesi et al.).

Non-limiting examples of methods for identifying such analytes include (i) cell-based binding methods for identifying analytes which bind the cS1P$_1$ receptor, inhibit or suppress binding between cS1P$_1$ receptor and its ligand, or interfere with the functional activation of Gα proteins via the cS1P$_1$ receptor in eukaryote cells and (ii) cell-free binding methods for identifying analytes which bind the cS1P$_1$ receptor, inhibit or suppress binding between the cS1P$_1$ receptor and its ligand, or interfere with the functional activation of Gα proteins via the cS1P$_1$ receptor. Thus, the present invention provides a means for identifying agonists and antagonists of the cS1P$_1$ receptor. The methods described herein are useful tools for identifying analytes which modulate molecular and/or functional interactions between the cS1P$_1$ receptor and its ligand or Gα proteins and, therefore, are modulators of the S1P$_1$-dependent signaling pathway.

The present invention is particularly useful for identifying analytes of pharmaceutical importance which can be used to design or develop therapies or treatments for diseases or disorders which involve modulation of S1P$_1$ receptor activity. Therefore, in one aspect of the present invention, an isolated nucleic acid molecule is provided which comprises a sequence of nucleotides encoding an RNA molecule that can be translated in vivo or in vitro to produce the cS1P$_1$ receptor with the amino acid sequence as set forth in SEQ ID NO:2 (FIG. 2). In further embodiments, the nucleic acid is substantially free from other nucleic acids of the dog or substantially free from other nucleic acids. In a further embodiment, the isolated nucleic acid molecule comprises the nucleotide sequence set forth in SEQ ID NO:1 (FIG. 1).

The isolated nucleic acid molecules include both deoxyribonucleic acid (DNA) and ribonucleic acid (RNA) molecules encoding the cS1P$_1$ receptor. The isolated nucleic-acid molecules further include genomic DNA and complementary DNA (cDNA) encoding the cS1P$_1$ receptor, either of which can be single- or double-stranded, as well as synthetic DNA, such as a synthesized, single stranded polynucleotide. When single-stranded, the DNA molecule can comprise either the coding (sense) strand or the non-coding (antisense) strand. For most cloning purposes, DNA is a preferred nucleic acid.

In further aspects of the present invention, modified cS1P$_1$ receptors are provided which have an amino acid sequence which is substantially similar to the amino acid sequence set forth in SEQ ID NO:2 and nucleic acids which encode the cS1P$_1$ receptor for use in the analyte screening assays disclosed herein. Further provided are nucleic acids encoding the cS1P$_1$ receptor which have a nucleotide sequence substantially similar to the nucleotide sequence set forth in SEQ ID NO:1. As used herein, the term "substantially similar" with respect to SEQ ID NO:2 means that the cS1P$_1$ receptor contains mutations such as amino acid substitution or deletion mutations that do not abrogate the ability of the cS1P$_1$ receptor to bind its ligand. The mutations include naturally occurring allelic variants and variants produced by recombinant DNA methods. As used herein, the term "substantially similar" with respect to SEQ ID NO:1 means that the cS1P$_1$ receptor encoded by the nucleic acid contains mutations such as nucleotide substitution or deletion mutations which do not abrogate the ability of the cS1P$_1$ receptor to bind its ligand. The mutations include naturally occurring allelic variants and variants produced by recombinant DNA methods. In general, any of the foregoing mutations which do not abrogate the ability of the cS1P$_1$ receptor to bind its ligand S1P are conservative mutations.

The present invention further includes biologically active mutants of SEQ ID NO:1. In general, any such biologically active mutant will encode either a polypeptide which has properties or activity substantially similar to the properties or activity of the cS1P$_1$ receptor, including but not limited to the cS1P$_1$ receptor as set forth in SEQ ID NO:2. Any such polynucleotide includes, but is not limited to, nucleotide substitutions, deletions, additions, amino-terminal truncations, and carboxy-terminal truncations which do not substantially abrogate the properties or activities of the cS1P$_1$ receptor produced therefrom. Thus, the mutations of the present invention encode mRNA molecules that express a cS1P$_1$ receptor in a eukaryotic cell which has sufficient activity (ability to bind one or more of its receptors) to be useful in drug discovery. Further, the present invention provides biologically active fragments of SEQ ID NO:2 and mutants thereof and the DNA encoding such fragments. The biologically active fragments can include any combination of the ligand binding domain, transmembrane domain, and G protein binding domain. For example, the biologically active fragment can consist of the ligand binding domain and the transmembrane domain.

The present invention further includes synthetic DNAs (sDNA) which encode the cS1P$_1$ receptor wherein the nucleotide sequence of the sDNA differs from the nucleotide sequence of SEQ ID NO:1 but still encodes cS1P$_1$ receptor as set forth in SEQ ID NO:2 or mutant with substantially similar properties or activity. For example, to express or enhance expression of the cS1P$_1$ receptor in a particular cell type, it may be necessary to change the sequence comprising one or more of the codons encoding the cS1P$_1$ receptor to sequences to enable expression of the cS1P$_1$ receptor in the particular cell type. Such changes include modifications for codon usage peculiar to a particular host or removing cryptic cleavage or regulatory sites which would interfere with expression of the cS1P$_1$ receptor in a particular cell type. Therefore, the present invention discloses codon redundancies which may result in numerous DNA molecules expressing an identical protein. For purposes of this specification, a sequence bearing one or more replaced codons will be defined as a degenerate variation. Also included within the scope of this invention are mutations either in the DNA sequence or the translated protein that do not alter or do not substantially alter the ultimate physical or functional properties of the expressed protein (in general, these mutations are referred to as conservative mutations). For example, substitution of valine for leucine, arginine for lysine, or asparagine for glutamine may not cause a change in the functionality of the polypeptide.

Included in the present invention are DNA sequences that hybridize to SEQ ID NO:1 under stringent conditions. By way of example, and not limitation, a procedure using conditions of high stringency is as follows. Prehybridization of filters containing DNA is carried out for about 2 hours to overnight at about 65° C. in buffer composed of 6×SSC, 5× Denhardt's solution, and 100 µg/mL denatured salmon sperm DNA. Filters are hybridized for about 12 to 48 hrs at 65° C. in prehybridization mixture containing 100 µg/mL denatured salmon sperm DNA and labeled DNA (for example, 5–20× $10^6$ cpm of $^{32}$P-labeled DNA). The filters are washed at 37° C. for about 1 hour in a solution containing 2×SSC, 0.1% SDS. This is followed by a wash in 0.1×SSC, 0.1% SDS at 50° C. for 45 minutes before autoradiography. Other procedures using conditions of high stringency would include either a hybridization step carried out in 5×SSC, 5× Denhardt's solution, 50% formamide at about 42° C. for about 12 to 48 hours or a washing step carried out in 0.2×SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). In addition to the foregoing, other conditions of high stringency which may be used are also well known in the art.

In an another aspect of the present invention, a substantially purified form of a cS1P$_1$ receptor which comprises a sequence of amino acids as disclosed in FIG. 2 (SEQ ID NO:2) is provided. Further provided are biologically active fragments and/or mutants of the cS1P$_1$ receptor, which comprise at least a portion of the amino acid sequence set forth in SEQ ID NO: 2. These mutations or fragments include, but not limited to, amino acid substitutions, deletions, additions, amino terminal truncations, and carboxy-terminal truncations such that these mutations provide for proteins or protein fragments of diagnostic, therapeutic, or prophylactic use and are useful for screening assays for identifying analytes that interfere with the interaction of the cS1P$_1$ receptor and its ligand, such analytes being useful for treatment of diseases or disorders which involve modulation of cS1P$_1$ receptor activity. In a particular embodiment, the present invention provides an isolated nucleic acid molecule comprising a sequence that encodes a mutated cS1P$_1$ receptor comprising the sequence set forth in SEQ ID NO:2 with about 1 to 10 amino acid additions, deletions, or substitutions, wherein the mutated cS1P$_1$ receptor polypeptide is capable of binding its S1P ligand.

The cS1P$_1$ receptors of the present invention can be the "mature" protein or a fragment or portion thereof (e.g., ligand binding domain, transmembrane domain, or G protein binding domain), any of which can be a part of a larger protein such as a fusion protein. It is often advantageous to include covalently linked to the amino acid sequence of the cS1P$_1$ receptor, an additional amino acid sequence which contains secretory or leader sequences, pro-sequences, sequences which aid in purification of the cS1P$_1$ receptors such as multiple histidine residues (polyHis) or antibody-binding epitopes, or one or more additional amino acid sequences which confer stability to the cS1P$_1$ receptor during recombinant production. Thus, cS1P$_1$ receptor fusion proteins are provided which comprise all or part of the cS1P$_1$ receptor linked at its amino or carboxyl terminus to proteins or polypeptides such as green fluorescent protein (GFP), c-myc epitope, alkaline phosphatase, protein A or G, glutathione S-transferase (GST), polyHis, peptide cleavage site, or antibody Fc region. Any such fusion construct can be expressed in a cell line of interest and used to screen for modulators of the cS1P$_1$ receptor disclosed herein. In a particular embodiment, the present invention provides an isolated nucleic acid molecule comprising a sequence that encodes a fusion CS1P$_1$ receptor comprising the sequence set forth in SEQ ID NO:2 or a fusion protein with amino acid additions, deletions, or substitutions, wherein the mutated cS1P$_1$ receptor is capable of binding its S1P ligand.

The present invention further provides vectors which comprise at least one of the nucleic acid molecules disclosed throughout this specification, preferably wherein the nucleic acid molecule is operably linked to a heterologous promoter. These vectors can comprise DNA or RNA. For most cloning purposes, DNA plasmid or viral expression vectors are preferred. Typical expression vectors include plasmids, modified viruses, bacteriophage, cosmids, yeast artificial chromosomes, and other forms of episomal or integrated DNA, any of which expresses the cS1P$_1$ receptor, polypeptide fragment thereof, or fusion protein comprising all or part of the cS1P$_1$ receptor encoded therein. It is well within the purview of the skilled artisan to determine an appropriate vector for a particular gene transfer or other use. As used herein, the term "recombinant cS1P$_1$ receptor" is intended to include any variation of cS1P$_1$ receptor disclosed herein which is expressed from a vector transfected into a eukaryote cell or transformed into a prokaryote cell. Transfected eukaryote cells and transformed prokaryote cells are referred to as recombinant host cells.

An expression vector containing DNA encoding a cS1P$_1$ receptor or any one of the aforementioned variations thereof wherein the DNA is preferably operably linked to a heterologous promoter can be used for expression of the recombinant cS1P$_1$ receptor in a recombinant host cell. Such recombinant host cells can be cultured under suitable conditions to produce recombinant cS1P$_1$ receptor or a biologically equivalent form, for example, as shown in the Examples. Expression vectors include, but are not limited to, cloning vectors, modified cloning vectors, specifically designed plasmids, or specifically designed viruses.

Commercially available mammalian expression vectors which are suitable for recombinant cS1P$_1$ receptor expression include, but are not limited to, pcDNA3.neo (Invitrogen, Carlsbad, Calif.), pcDNA3.1 (Invitrogen, Carlsbad, Calif.), pcDNA3.1/Myc-His (Invitrogen), pCI-neo (Promega, Madison, Wis.), pLITMUS28, pLITMUS29, pLITMUS38 and pLITMUS39 (New England Biolabs, Beverly, Mass.), pcDNAI, pcDNAIamp (Invitrogen), pcDNA3 (Invitrogen), pMC1neo (Stratagene, La Jolla, Calif.), pXT1 (Stratagene), pSG5 (Stratagene), EBO-pSV2-neo (ATCC 37593) pBPV-1 (8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also, a variety of bacterial expression vectors can be used to express recombinant $cS1P_1$ receptor in bacterial cells. Commercially available bacterial expression vectors which may be suitable for recombinant $cS1P_1$ receptor expression include, but are not limited to, pCR2.1 (Invitrogen), pET11a (Novagen, Madison, Wis.), lambda gt11 (Invitrogen), and pKK223-3 (Pharmacia).

In addition, a variety of fungal cell expression vectors may be used to express recombinant $cS1P_1$ receptor in fungal cells. Commercially available fungal cell expression vectors which are suitable for recombinant $cS1P_1$ receptor expression include, but are not limited to, pYES2 (Invitrogen) and *Pichia* expression vector (Invitrogen).

Also, a variety of insect cell expression vectors can be used to express recombinant $cS1P_1$ receptor in insect cells. Commercially available insect cell expression vectors which can be suitable for recombinant expression of $cS1P_1$ receptor include, but are not limited to, pBlueBacIII and pBlueBacHis2 (Invitrogen), and pAcG2T (Pharmingen).

Viral vectors which can be used for expression of recombinant $cS1P_1$ receptor include, but are not limited to, adenovirus vectors, adeno-associated virus vectors, herpesvirus vectors, Sindbis virus vectors, Simliki forest virus vectors, pox virus vectors (such as vaccinia virus, fowl pox, canary pox, and the like), retrovirus vectors, and baculovirus vectors. Many of viral vectors are commercially available.

The nucleic acids of the present invention in the above vectors for expressing the $S1P_1$ or fragment thereof are preferably assembled into an expression-cassette that comprises sequences which provide for efficient expression of the $cS1P_1$ receptor or variant thereof encoded thereon in a eukaryote cell, preferably a mammalian cell such as a CHO cell or variant thereof. The cassette preferably contains the full-length cDNA encoding the $cS1P_1$ receptor or a DNA encoding a fragment of the $cS1P_1$ receptor with homologous or heterologous transcriptional and translational control sequences operably linked to the DNA. Such control sequences include at least a transcription promoter (constitutive or inducible) and transcription termination sequences and can further include other regulatory elements such as transcription enhancers, ribosome binding sequences, splice junction sequences, and the like. In most embodiments, the promoter is a heterologous promoter; however, in particular embodiments, the promoter can be the natural $cS1P_1$ receptor promoter. In either embodiment, the expression cassette allows for ectopic expression of the $cS1P_1$ receptor in various host cells of non-canine origin. In a particularly useful embodiment, the promoter is the constitutive cytomegalovirus immediate early promoter with or without the intron A sequence ($CMV_{ie}$ promoter) although those skilled in the art will recognize that any of a number of other known promoters such as the strong immunoglobulin promoter, Rous sarcoma virus long terminal repeat promoter, SV40 small or large T antigen promoter, or the like. A transcriptional terminator can be the bovine growth hormone terminator although other known transcriptional terminators such as SV40 termination sequences can also be used.

The present invention further provides recombinant host cells transformed or transfected with a vector comprising any one of the aforementioned nucleic acid molecules, particularly host cells transformed or transfected with a vector comprising any one of the aforementioned nucleic acid molecules wherein the nucleic acid molecule is operably linked to a promoter. Recombinant host cells include bacteria such as *E. coli*, fungal cells such as yeast, plant cells, mammalian cells including, but not limited to, cell lines of bovine, porcine, monkey, human, or rodent origin; and insect cells including, but not limited to, *Drosophila* and silkworm-derived cell lines. For instance, one insect expression system utilizes *Spodoptera frugiperda* (Sf21) insect cells (Invitrogen) in tandem with a baculovirus expression vector (pAcG2T, Pharmingen, San Diego, Calif.). Mammalian cells which may be suitable and which are commercially available, include but are not limited to, L cells L-M (TK-) (ATCC CCL-1.3), L cells L-M (ATCC CCL-1.2), Saos-2 cells (ATCC HTB-85), 293 cells (ATCC CRL-1573), Raji cells (ATCC CCL-86), CV-1 cells (ATCC CCL-70), COS-1 cells (ATCC CRL-1650), COS-7 cells (ATCC CRL-1651), CHO-K1 cells (ATCC CCL-61), 3T3 cells (ATCC CCL-92), NIH/3T3 cells (ATCC CRL-1658), HeLa cells (ATCC CCL-2), C127I cells (ATCC CRL-1616), BS-C-1 cells (ATCC CCL-26), MRC-5 cells (ATCC CCL-171), HEK293T cells (ATCC CRL-1573), ST2 cells (Riken Cell bank, Tokyo, Japan RCB0224), C3H10T1/2 cells (JCRB0602, JCRB9080, JCRB0003, or IFO50415), and CPAE cells (ATCC CCL-209). Such recombinant host cells can be cultured under suitable conditions to produce $cS1P_1$ receptor or a biologically equivalent form. Recombinant eukaryote cells include both transiently infected cells and stably transfected cells in which the expression cassette or vector is integrated into the genome of the cell.

As noted above, an expression vector containing DNA encoding $cS1P_1$ receptor or any one of the aforementioned variations thereof can be used to express the $cS1P_1$ receptor encoded therein in a recombinant host cell. Therefore, the present invention provides a process for expressing a $cS1P_1$ receptor or any one of the aforementioned variations thereof in a recombinant host cell comprising introducing the vector comprising a nucleic acid that encodes the $cS1P_1$ receptor into a suitable host cell and culturing the host cell under conditions which allow expression of the $cS1P_1$ receptor and preferably, integration of the $cS1P_1$ receptor into the cell's membrane. In a further embodiment, the $cS1P_1$ receptor has an amino acid sequence substantially as set forth in SEQ ID NO:2 and binds at least its ligand S1P, and the nucleic acid encoding the $cS1P_1$ receptor is operably linked to a heterologous promoter which can be constitutive or inducible. Thus, the present invention further provides a cell comprising a nucleic acid encoding the $cS1P_1$ receptor which has an amino acid sequence substantially as set forth in SEQ ID NO:2, which preferably binds at least its ligand S1P, and wherein the nucleic acid encoding the cS1P$_1$ receptor is operably linked to a heterologous promoter.

Following expression of cS1P$_1$ receptor or any one of the aforementioned variations of the cS1P$_1$ receptor in a host cell, cS1P$_1$ receptor or variant thereof can be recovered to provide cS1P$_1$ receptor in a form capable of binding to its ligand. Several cS1P$_1$ receptor purification procedures are available and suitable for use. The cS1P$_1$ receptor can be purified from cell lysates and extracts by various combinations of, or individual application of, salt fractionation, ion exchange chromatography, size exclusion chromatography, hydroxylapatite adsorption chromatography, or hydrophobic interaction chromatography. In addition, cS1P$_1$ receptor can be separated from other cellular polypeptides by use of an immunoaffinity column made with monoclonal or polyclonal antibodies specific for cS1P$_1$ receptor or a particular epitope thereof. Alternatively, in the case of fusion polypeptides comprising all or a portion of the cS1P$_1$ receptor fused to a second polypeptide, purification can be achieved by affinity chromatography comprising a reagent specific for the second polypeptide such as an antibody or metal.

Cloning, expression vectors, transfections and transformations, and protein isolation of expressed proteins are well known in the art and have been described, for example, in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). For example, any of a variety of procedures may be used to clone DNA encoding cS1P$_1$ receptor from RNA isolated from the dog. These methods include, but are not limited to, the method shown in Examples 1-3 and the following methods.

(1) RACE PCR cloning methods such as disclosed in Frohman et al., Proc. Natl. Acad. Sci. USA 85: 8998-9002 (1988)). 5' and/or 3' RACE can be performed to generate a full-length cDNA sequence. This strategy involves using gene-specific oligonucleotide primers for PCR amplification of cS1P$_1$ receptor cDNA. These gene-specific primers are designed through identification of an expressed sequence tag (EST) nucleotide sequence which has been identified by searching any number of publicly available nucleic acid and protein databases.

(2) Direct functional expression of the cS1P$_1$ receptor cDNA following the construction of a cS1P$_1$ receptor containing cDNA library in an appropriate expression vector system.

(3) Screening a cS1P$_1$ receptor-containing cDNA library constructed in a bacteriophage or plasmid shuttle vector with a labeled degenerate oligonucleotide probe designed from the amino acid sequence of the cS1P$_1$ receptor.

(4) Screening a cS1P$_1$ receptor-containing cDNA library constructed in a bacteriophage or plasmid shuttle vector with a partial cDNA encoding the cS1P$_1$ receptor. This partial cDNA is obtained by the specific PCR amplification of cS1P$_1$ receptor DNA fragments through the design of degenerate oligonucleotide primers from the amino acid sequence known for other membrane proteins which are related to the cS1P$_1$ receptor.

(5) Screening a cS1P$_1$ receptor-containing cDNA library constructed in a bacteriophage or plasmid shuttle vector with a partial cDNA or oligonucleotide with homology to a mammalian cS1P$_1$ receptor protein. This strategy may also involve using gene-specific oligonucleotide primers for PCR amplification of cS1P$_1$ receptor cDNA identified as an EST as described above.

(6) Designing 5' and 3' gene specific oligonucleotides using SEQ ID NO: 1 as a template so that either the full-length cDNA can be generated by known RACE techniques or a portion of the coding region can be generated by these same known RACE techniques to generate and isolate a portion of the coding region to use as a probe to screen one of numerous types of cDNA and/or genomic libraries in order to isolate a full-length version of the nucleotide sequence encoding cS1P$_1$ receptor.

It would be readily apparent to those skilled in the art that other types of libraries, as well as libraries constructed from other cell types or species types, may be useful for isolating a cS1P$_1$ receptor-encoding DNA or a cS1P$_1$ receptor homologue. Other types of libraries include, but are not limited to, cDNA libraries derived from other cells. The selection of cells or cell lines for use in preparing a cDNA library to isolate a cDNA encoding cS1P$_1$ receptor can be done by first measuring cell-associated cS1P$_1$ receptor activity using any known assay available for such a purpose.

Preparation of cDNA Libraries can be Performed by Standard Techniques Well Known in the art. Well known cDNA library construction techniques can be found for example, in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). Complementary DNA libraries may also be obtained from numerous commercial sources, including but not limited to Clontech Laboratories, Inc. (Palo Alto, Calif.) and Stratagene (La Jolla, Calif.).

The DNA molecules, RNA molecules, and recombinant polypeptides of the present invention can be used to screen and measure levels of cS1P$_1$ receptor expression in homologous or heterologous cells. The recombinant polypeptides, DNA molecules, and RNA molecules lend themselves to the formulation of kits suitable for the detection and typing of cS1P$_1$ receptors. Such a kit would comprise a compartmentalized carrier suitable to hold in close confinement at least one container. The carrier would further comprise reagents such as recombinant cS1P$_1$ receptor or anti-cS1P$_1$ receptor antibodies suitable for detecting cS1P$_1$ receptors. The carrier may also contain a means for detection such as labeled antigen or enzyme substrates or the like. The kit enables identification of polymorphic forms of cS1P$_1$ receptor which can then be used in the previously described methods to determine the effect the polymorphism has on binding between the polymorphic cS1P$_1$ receptor and its ligand.

In accordance with yet another embodiment of the present invention, there are provided antibodies having specific affinity for the cS1P$_1$ receptor or epitope thereof. The term "antibodies" is intended to be a generic term which includes polyclonal antibodies, monoclonal antibodies, Fab fragments, single V$_H$ chain antibodies such as those derived from a library of camel or llama antibodies or camelized antibodies (Nuttall et al., Curr. Pharm. Biotechnol. 1: 253-263 (2000); Muyldermans, J. Biotechnol. 74: 277-302 (2001)), and recombinant antibodies. The term "recombinant antibodies" is intended to be a generic term which includes single polypeptide chains comprising the polypeptide sequence of a whole heavy chain antibody or only the amino terminal variable domain of the single heavy chain antibody (V$_H$ chain polypeptides) and single polypeptide chains comprising the variable light chain domain (V$_L$) linked to the variable heavy chain domain (V$_H$) to provide a single recombinant polypeptide comprising the Fv region of the antibody molecule (scFv polypeptides) (See, Schmiedl et al., J. Immunol. Meth. 242:

101-114 (2000); Schultz et al., Cancer Res. 60: 6663-6669 (2000); Dübel et al., J. Immunol. Meth. 178: 201-209 (1995); and in U.S. Pat. No. 6,207,804 B1 to Huston et al.). Construction of recombinant single $V_H$ chain or scFv polypeptides which are specific against an analyte can be obtained using currently available molecular techniques such as phage display (de Haard et al., J. Biol. Chem. 274: 18218-18230 (1999); Saviranta et al., Bioconjugate 9: 725-735 (1999); de Greeff et al., Infect. Immun. 68: 3949-3955 (2000)) or polypeptide synthesis. In further embodiments, the recombinant antibodies include modifications such as polypeptides having particular amino acid residues or ligands or labels such as horseradish peroxidase, alkaline phosphatase, fluors, and the like. Further still embodiments include fusion polypeptides which comprise the above polypeptides fused to a second polypeptide such as a polypeptide comprising protein A or G.

The antibodies specific for $cS1P_1$ receptor can be produced by methods known in the art. For example, polyclonal and monoclonal antibodies can be produced by methods well known in the art, as described, for example, in Harlow and Lane, Antibodies: A Laboratory Manual. Cold Spring Harbor Laboratory Press: Cold Spring Harbor, N.Y. (1988). The $cS1P_1$ receptor or fragments thereof can be used as immunogens for generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, camelized, CDR-grafted, or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (See, for example, Bahouth et al., Trends Pharmacol. Sci. 12: 338 (1991); Ausubel et al., Current Protocols in Molecular Biology (John Wiley and Sons, N.Y. (1989)).

Antibodies so produced can be used for the immunoaffinity or affinity chromatography purification of the $cS1P_1$ receptor or $cS1P_1$ receptor/ligand complexes. The above referenced anti-$cS1P_1$ receptor antibodies can also be used to modulate the activity of the $cS1P_1$ receptor in living animals, in humans, or in biological tissues isolated therefrom. Accordingly, contemplated herein are compositions comprising a carrier and an amount of an antibody having specificity for $cS1P_1$ receptor effective to block naturally occurring $cS1P_1$ receptor from binding its ligand.

Therefore, the nucleic acids encoding $cS1P_1$ receptor or variant thereof, vectors containing the same, host cells transformed with the nucleic acids or vectors which express the $cS1P_1$ receptor or variants thereof, the $cS1P_1$ receptor and variants thereof, as well as antibodies specific for the $cS1P_1$ receptor, can be used in in vivo or in vitro methods for screening a plurality of analytes to identify analytes that are modulators of the $cS1P_1$ receptor/ligand interaction. These methods provide information regarding the function and activity of the $cS1P_1$ receptor and variants thereof which can lead to the identification and design of molecules, compounds, or compositions capable of specific interactions with canine and ultimately, the human $cS1P_1$ receptor. In preferred embodiments, the methods identify analytes which interfere with the binding of the $cS1P_1$ receptor to its ligand or activity of the $cS1P_1$ receptor. Such analytes are useful either alone or in combination with other compounds for treating a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves opthalmopathy, atopic dermatitis, and asthma; and, as part of chemotherapeutic regimens for the treatment of cancers, lymphomas, and leukemias, and in organ transplantation. Accordingly, the present invention provides methods (screening assays) for identifying analytes that modulate the binding of $cS1P_1$ receptor to its ligand or activity of the $cS1P_1$ receptor and which can be used for treating the aforementioned diseases or disorders. The method involves identifying analytes that bind to the $cS1P_1$ receptor and/or have a stimulatory or inhibitory effect on the biological activity of the $cS1P_1$ receptor or its expression and then determining which of these analytes has an effect on symptoms or diseases regarding the aforementioned disorders and diseases in an in vivo assay.

The screening assays include (i) cell-based methods for identifying analytes which bind the $cS1P_1$ receptor, inhibit or suppress binding between $cS1P_1$ receptor and its ligand, or modulate activity of the $cS1P_1$ receptor, and (ii) cell-free methods for identifying analytes which bind the $cS1P_1$ receptor, inhibit or suppress binding between the $cS1P_1$ receptor and its ligand, or modulate activity of the $cS1P_1$ receptor. Analytes that bind or modulate activity of the $cS1P_1$ receptor include both agonists and antagonists. Thomsen et al., Curr. Drug. Discovery, January: 13-18 (2004), provide a review of screening assays for identifying modulators of G-protein-coupled receptors, any one of which can be used to identify modulators of the $cS1P_1$ receptor.

Cell-based methods for identifying analytes that bind or modulate the activity of the $cS1P_1$ receptor can be accomplished by any method suitable for measuring the activity of mammalian $S1P_1$ receptors, which include for example, many methods suitable for measuring the activity of a G-protein-coupled receptor or any other seven transmembrane receptor. Methods for measuring activity of G-protein coupled receptors (functional assays) include, but are not limited to, measuring alterations in the concentration of intracellular $Ca^{2+}$, inositol triphosphate ($IP_3$), diacylglycerol (DAG), or adenosine cyclic 3',5'-monophosphate (cAMP) in response to an analyte; activation of phospholipase C or protein kinase C (PKC), or alterations in the concentration or activation of other signaling molecules.

Analytes that bind the $cS1P_1$ receptor can be identified in a competitive binding cell-based assay using cells which express the $cS1P_1$ on the cell surface and labeled-S1P as a competitor. Example 3 illustrates a competitive cell-based binding assay. In a typical competitive binding assay, eukaryote cells which have been transiently or stably transfected with an expression vector that expresses the $cS1P_1$ receptor are incubated in a cell culture medium suitable for the cells for a time sufficient for the $cS1P_1$ receptor to become integrated into the membranes of the cells. The cells can be adherent cells or non adherent cells. For example, the cells can be adherent cells such as CHO cells which are incubated in cell culture dishes in a medium suitable for growing the CHO cells such that the CHO cells grow in the culture dishes as a monolayer. Alternatively, the cells can be non-adherent cells such as HeLa S cells which are incubated in culture bottles under agitation, e.g., spinner culture bottles. After sufficient time has elapsed to allow a significant number of $cS1P_1$ receptors to be expressed and become integrated into the membranes of the cells, the cells are harvested. In the case of adherent cells, the transfected cells are harvested with an enzyme-free dissociation solution to dislodge the cells from the surface of the tissue culture dishes without causing damage to the $cS1P_1$ integrated into the membranes of the cells. The cells are pelleted by low speed centrifugation and suspended in a buffer. Aliquots of the cells are transferred to buffer containing labeled S1P and analyte to be tested. After incubating for a time sufficient for S1P and/or analyte to bind the $cS1P_1$, unbound labeled S1P and analyte are removed and the amount of labeled S1P is then detected by a method suitable for detecting the label. Non-specific binding can be defined as the amount of label bound to the $cS1P_1$ receptor on the cells in the presence of an excess of unlabeled S1P (e.g., about 200 nM unlabeled S1P).

In variations of the assay, a plurality of cell aliquots are mixed with aliquots of the mixture containing different concentrations of the analyte to be tested. Analytes which cause a decrease in the amount of label retained relative to controls comprising the labeled S1P and no analyte are analytes that bind to the $cS1P_1$ receptor. Serial dilutions of the analyte in the presence of a fixed amount of labeled S1P enable the affinity of the analyte for the $cS1P_1$ receptor to be determined. In an alternative embodiment of the above assay, the S1P is unlabeled and the analyte is labeled. In this case, analytes which bind the $cS1P_1$ receptor are determined by detecting the amount of labeled analyte bound in the absence and presence of various concentrations of S1P. In a further alternative of the competitive binding assay, the assay is performed as a cell-free assay wherein membranes comprising the $cS1P_1$ receptor are prepared as described below and incubated with S1P and analyte as above.

In the assays disclosed herein, determination of the amount of binding in the presence of varying concentrations of analyte and S1P and analysis of the data by a computer program such as the PRISM software (GraphPad Software, Inc. San Diego, Calif.) can be used to measure the affinity of the analyte for the $cS1P_1$ receptor. Specificity of analytes for the $cS1P_1$ receptor can be determined by measuring the level of labeled S1P binding in the presence of the analyte to related S1P receptors ($S1P_1$, $S1P_2$, $S1P_3$, $S1P_4$, $S1P_5$, canis or non-canis) in similar binding assays using membranes prepared from cells transfected with each respective receptor.

Analytes that can bind to the $cS1P_1$ receptor and which can act as an agonist or antagonist can be determined in a functional or signaling assay. Examples of cell-based functional assays include, but are not limited to, measuring alterations in the concentration of intracellular $Ca^{2+}$ (calcium flux), inositol triphosphate ($IP_3$), diacylglycerol (DAG), or adenosine cyclic 3',5'-monophosphate (cAMP) in response to an analyte; or activation of phospholipase C (PLC) or protein kinase C (PKC) in response to an analyte.

Measuring calcium flux in response to an analyte can be used to identify analytes that are G-protein-coupled receptor agonists or antagonists. Binding of a ligand to a G-protein-coupled receptor coupled to $G\alpha_q$ activates $PLC_\beta$. The $PLC_\beta$ hydrolyzes $PIP_2$ to DAG and $IP_3$. The $IP_3$ then acts to effect an increase in intracellular concentrations of $Ca^{2+}$ via release of the $Ca^{2+}$ from intracellular $Ca^{2+}$ stores. DAG can activate specific-protein-kinase C (PKC) isoforms such $PKC\alpha$ and $PK\beta$. The increase in intracellular $Ca^{2+}$ can be conveniently assessed using fluorescence-based $Ca^{2+}$ release measurements. The $cS1P_1$ receptor is primarily a $G\alpha_{i/o}$-coupled receptor which in the presence of a ligand can also stimulate $Ca^{2+}$ release (Okamoto et al., J. Biol. Chem. 273: 27104-27110 (1998). Therefore, in a further aspect of the present invention, a gene expression cassette encoding the $cS1P_1$ receptor is transfected into eukaryote cells such as CHO K1 cells. An aliquot of the cotransfected cells is then incubated in a medium containing an analyte, an aliquot with a known agonist as a positive control, and an aliquot with neither the analyte nor the agonist as a negative control. Each of the aliquots further comprises a means for detecting release of $Ca^{2+}$ from intracellular $Ca^{2+}$ stores. Such means include further cotransfecting into the cell a gene expression cassette encoding aequorin, which in the presence of $Ca^{2+}$, emits photons that are detectable with a luminometer, or including a calcium-sensitive dye such as fluor-3 or fluor-4 which fluoresces in the presence of $Ca^{2+}$ and which fluorescence is detectable with a fluorometer. An analyte that is an agonist causes a detectable increase in the release of $Ca^{2+}$ from the intracellular stores. To detect an analyte which is an antagonist, aliquots of the cells are incubated in a serial dilution of the analyte in a medium and the $Ca^{2+}$ flux measured for each of the aliquots. Then, to each of the aliquots, an agonist is added and the $Ca^{2+}$ flux measured. An antagonist results in a decrease in the release of $Ca^{2+}$ from the intracellular stores in the presence of the known agonist. WO0168922 to Grant et al. discloses a high throughput calcium flux assay for G-protein-coupled receptors.

While the $S1P_1$ receptor can stimulate $Ca^{2+}$ release, it has been found that the stimulation can be enhanced by coexpressing the $S1P_1$ receptor with a chimeric G protein such as $G\alpha_{qo5}$ or $G\alpha_{q55}$ or co-expressing with certain promiscuous G proteins such as $G\alpha_{15}$ or $G\alpha_{16}$. The G proteins are capable of interacting with $G\alpha_{i/o}$ and $G\alpha_q$ and allowing an increase in the intracellular $Ca^{2+}$ response to an agonist. Assays that link $G\alpha_{i/o}$-coupled receptors to calcium flux have been described by Coward et al., Anal. Biochem. 270: 242-249 (1999), Kazmi et al., Biochem. 39: 3734-3744 (2000), Gopalakrishnan et al., Anal. Biochem. 321: 192-201 (2003); and Knight et al., Anal. Biochem. 320: 88-103 (2003).

Therefore, in a further aspect of the present invention, a first gene expression cassette encoding the $cS1P_1$ receptor is cotransfected with a second gene expression cassette encoding a chimeric or promiscuous G protein into eukaryote cells. An aliquot of the cotransfected cells is then incubated in a medium containing an analyte, an aliquot with a known agonist as a positive control, and an aliquot with neither the analyte nor the agonist as a negative control. Detecting release of $Ca^{2+}$ from intracellular $Ca^{2+}$ stores is as described above. An analyte which is an agonist causes a detectable increase in the release of $Ca^{2+}$ from the intracellular stores. To detect an analyte that is an antagonist, aliquots of the cells are incubated in a serial dilution of the analyte in a medium and the $Ca^{2+}$ flux measured for each of the aliquots. Then, to each of the aliquots, an agonist is added and the $Ca^{2+}$ flux measured.

Agonists or antagonists of the $cS1P_1$ receptor can be identified by measuring the change in $IP_3$ or DAG concentrations or activity of PKC in response to an analyte. The $IP_3$ or DAG can be measured using antibodies specific for the $IP_3$ or the DAG. Commercially available assays for measuring $IP_3$ include HITHUNTER (DiscoveRx Corp., Freemont, Calif.) and ALPHASCREEN IP3 (Perkin Elmer Life and Analytical, Boston, Mass.). WO2003021220 to Brandish and Hill describes an assay for measuring inositol phosphate concentrations. Commercially available assays for measuring DAG include the BIOTRAK DAG Assay (Amersham Bioscience, Piscataway, N.J.). Commercially available assays for measuring PKC activity include the RPN77 Protein Kinase C BIOTRAK Assay System (Amersham Bioscience).

Therefore, in a further aspect of the present invention, a gene expression cassette encoding the $cS1P_1$ receptor is transfected into eukaryote cells such as CHO K1 cells. An aliquot of the cotransfected cells is then incubated in a medium containing an analyte, an aliquot with a known agonist as a positive control, and an aliquot with neither the analyte nor the agonist as a negative control. Each of the aliquots further comprises a means for detecting $IP_3$ or DAG. An agonist results in an increase in $IP_3$ or DAG levels relative to the negative control. To detect an analyte that is an antagonist, aliquots of the cells are incubated in a serial dilution of the analyte in a medium and $IP_3$ or DAG measured for each of the aliquots. Then, to each of the aliquots, an agonist is added and the $IP_3$ or DAG measured. An antagonist results in a decrease in $IP_3$ or DAG levels in the presence of the known agonist.

To enhance the stimulation of $PLC_\beta$ activity on $PIP_2$, the first gene expression cassette encoding the $cS1P_1$ receptor is cotransfected with a second gene expression cassette encoding a chimeric or promiscuous G protein into eukaryote cells. An aliquot of the cotransfected cells are then incubated in a medium containing an analyte, an aliquot with a known agonist as a positive control, and an aliquot with neither the analyte nor the agonist as a negative control. Each of the aliquots further comprise a means for detecting $IP_3$ or DAG as described above. An analyte which is an agonist causes a detectable increase in $IP_3$ or DAG. To detect an analyte that is an antagonist, aliquots of the cells are incubated in a serial dilution of the analyte in a medium and the $IP_3$ or DAG measured for each of the aliquots. Then, to each of the aliquots, an agonist is added and the $IP_3$ or DAG measured.

Agonists or antagonists of the $cS1P_1$ receptor can also be identified by measuring activation of the $PLC_\beta$. Examples of assays for detecting $PLC_\beta$ activity include the following. Várnai and Balla, J. Cell. Biol. 143: 501-510 (1998) describe a method for measuring $PLC_\beta$ activation that uses a fusion protein consisting of the pleckstrin homology (PH) domain of $PLC\delta1$ fused to a green fluorescent protein (GFP). In the absence of $PLC_\beta$ activity, the fusion protein is associated with $PIP_2$ along the cytosol side of the cell membrane. In the presence of $PLC_\beta$ activity, the $PIP_2$ is hydrolyzed to DAG and $IP_3$, which releases the fusion protein to the cytosol. Van der Wal et al., J. Biol. Chem. 276: 15337-15344 (2001), describe a method for measuring $PLC_\beta$ activation that measures fluorescence resonance energy transfer (FRET) between PH domains in which one domain is tagged with a fluorescence donor and the other is tagged with a fluorescence acceptor. In the absence of PLC activity, the PH domains bind $PIP_2$ and because the acceptor and donor fluors are in close proximity, the fluorescence energy from the donor fluor is transferred to the acceptor fluor fluoresces at a first wavelength. In the presence of $PLC_\beta$ activity, the PH domains are released to the cytosol. Because the PH domains are no longer in close proximity, the donor fluor fluoresces at a second wavelength.

Therefore, in a further aspect of the present invention, a gene expression cassette encoding the $cS1P_1$ receptor is transfected into eukaryote cells such as CHO K1 cells. An aliquot of the cotransfected cells is then incubated in a medium containing an analyte, an aliquot with a known agonist as a positive control, and an aliquot with neither the analyte nor the agonist as a negative control. Each of the aliquots further comprises a means for detecting $PLC_\beta$ activity such as disclosed above. An analyte that is an agonist results in a detectable increase in $PLC_\beta$ activity with respect to the negative control. To detect an analyte that is an antagonist, aliquots of the cells are incubated in a serial dilution of the analyte in a medium and $PLC_\beta$ activity measured for each of the aliquots. Then, to each of the aliquots, an agonist is added and the $PLC_\beta$ activity measured. An antagonist results in a decrease in $PLC_\beta$ activity relative to the positive control in the presence of the known agonist.

To enhance the stimulation of the $PLC_\beta$ activity, the first gene expression cassette encoding the $cS1P_1$ receptor is cotransfected with a second gene expression cassette encoding a chimeric or promiscuous G protein into eukaryote cells. An aliquot of the cotransfected cells is then incubated in a medium containing an analyte, an aliquot with a known agonist as a positive control, and an aliquot with neither the analyte nor the agonist as a negative control. Each of the aliquots further comprise a means for detecting $PLC_\beta$ activity as disclosed above. To detect an analyte that is an antagonist, aliquots of the cells are incubated in a serial dilution of the analyte in a medium and the $PLC_\beta$ activity measured for each of the aliquots. Then, to each of the aliquots, an agonist is added and the $PLC_\beta$ activity measured.

Activation of $S1P_1$ receptors by S1P results in inhibition of adenylate cyclase activity with a concomitant decrease in cAMP levels. The decrease in cAMP levels results in a decrease in expression of genes regulated by a cAMP-responsive promoter. Agonists and antagonists of the $cS1P_1$ receptor can be identified in an assay that measures inhibition of adenylate cyclase via the decrease in cAMP. Chen et al., Anal. Biochem. 226: 349-354 (1995), describes a colorimetric assay that uses a recombinant cell transfected with an expression vector encoding a G-protein coupled receptor with a second expression vector containing a promoter with a cAMP responsive element operably linked to the β-galactosidase reporter gene. An alternative assay using enzyme fragment complementation to assay cAMP activity is described in Golla and Seethala, J. Biomol. Screen, 7: 515-525 (2002). Commercially available kits include HITHUNTER cAMF from DiscoveRx Corp. and cAMP DIRECT BIOTRAK kit (Amersham Biosciences). Other methods for measuring changes in cAMP levels are well known in the art.

Therefore, in a further aspect of the present invention, a first gene expression cassette encoding the $cS1P_1$ receptor and a second gene expression cassette encoding a reporter gene encoding an assayable product operably linked to a cAMP responsive promoter, i.e., a promoter comprising one or more cAMP response elements, are transfected into eukaryote cells such as CHO K1 cells. An aliquot of the cotransfected cells is then incubated in a medium containing an analyte, an aliquot with a known agonist as a positive control, and an aliquot with neither the analyte nor the agonist as a negative control. Each of the aliquots further comprises a means for detecting the reporter gene product. An agonist results in a reduction in expression of the reporter gene relative to the negative control. To detect an analyte that is an antagonist, aliquots of the cells are incubated in a serial dilution of the analyte in a medium and reporter gene expression measured for each of the aliquots. Then, to each of the aliquots, an agonist is added and reporter gene expression measured. An antagonist results in expression of the reporter gene relative to the positive control in the presence of the known agonist.

In a further still aspect, a first gene expression cassette encoding the $cS1P_1$ receptor, a second gene expression cassette encoding a reporter gene encoding an assayable product (e.g., a reporter gene encoding luciferase, β-lactamase, secreted alkaline phosphatase (SEAP), or the like) operably linked to a promoter comprising a cAMP response element, and a third gene expression cassette encoding a chimeric or promiscuous G protein are cotransfected into eukaryote cells. An aliquot of the cotransfected cells are then incubated in a medium containing an analyte, an aliquot with a known agonist as a positive control, and an aliquot with neither the analyte nor the agonist as a negative control. Each of the aliquots further comprises a means for detecting reporter gene expression as described above. To detect an analyte which is an antagonist, aliquots of the cells are incubated in a serial dilution of the analyte in a medium and reporter gene expression measured for each of the aliquots. Then, to each of the aliquots, an agonist is added and reporter gene expression measured.

In an alternative embodiment for measuring the effect on cAMP synthesis, a first gene expression cassette encoding the $cS1P_1$ receptor is transfected into eukaryote cells such as CHO K1 cells. An aliquot of the cotransfected cells is then incubated in a medium containing an analyte, an aliquot with a known agonist as a positive control, and an aliquot with neither the analyte nor the agonist as a negative control. The levels of cAMP are then measured using any one of a number of commercially available assays for measuring cAMP levels, e.g., the HITHUNTER cAMP kit or the cAMP DIRECT BIOTRAK kit (Amersham Biosciences).

Cell-free assays include contacting $cS1P_1$ receptor (or variant thereof, for example, full-length, a biologically active fragment thereof, or a fusion protein comprising all or a portion of the $cS1P_1$ receptor) with an analyte and determining the ability of the analyte to bind to the $S1P_1$ receptor or modulate activity of the $cS1P_1$ receptor. Binding of the analyte to the $cS1P_1$ receptor can be determined either directly or indirectly. In one aspect, the assay includes contacting the $cS1P_1$ receptor with a known analyte that binds the $cS1P_1$ receptor to form an assay mixture, contacting the assay mixture with an analyte, and determining the ability of the analyte to interact with the $cS1P_1$ receptor, wherein determining the ability of the analyte to interact with the $cS1P_1$ receptor comprises determining the ability of the analyte to preferentially bind to the $cS1P_1$ receptor as compared to an analyte which is known to bind the $cS1P_1$ receptor. Detection of binding can be direct, for example, wherein the analyte is labeled, or indirectly, for example, in competition assays wherein the analyte competes for binding to the $cS1P_1$ receptor with S1P or other analyte known to bind the S1P.

The cell-free assays of the present invention can use either a membrane-bound form of $cS1P_1$ receptor or a soluble fragment thereof. In the case of cell-free assays comprising the membrane-bound form of the $cS1P_1$ receptor, it may be desirable to use a solubilizing agent such that the membrane-bound form of the $cS1P_1$ receptor is maintained in solution. Examples of such solubilizing agents include but are not limited to non-ionic detergents such as n-octylglucoside, n-dodecyl glucoside, n-dodecylmaltoside, octanoyl-N-methylglucamide, decanoyl-N-methyl glucamide, Triton X-100, Triton X-114, Thesit, Isotridecypoly(ethylene glycol 5 ether)n, 3-[(3-cholamidopropyl)dimethylamminio]-1-propane sulfonate (CHAPS), 3[(3-cholamidopropyl)dimethylamminio]-2-hydroxy-1-propane sulfonate (CHAPSO), N-dodecyl=N, N-dimethyl-3-ammonio-1-propanesulfonate.

Analytes that bind the $cS1P_1$ receptor can be identified in a competitive binding cell-free assay using membranes from cells which express the $cS1P_1$ on the cell surface and labeled-S1P as a competitor. In a typical competitive binding assay, eukaryote cells, which have been transiently or stably transfected with an expression vector that expresses the $cS1P_1$ receptor, are incubated in a cell culture medium suitable for the cells for a time sufficient for the $cS1P_1$ receptor to become integrated into the membranes of the cells. The cells can be adherent cells or non adherent cells. For example, the cells can be adherent cells such as CHO cells which are incubated in cell culture dishes in a medium suitable for growing the CHO cells such that the CHO cells grow in the culture dishes as a monolayer. Alternatively, the cells can be non-adherent cells such as HeLa S cells which are incubated in culture bottles under agitation, e.g., spinner culture bottles. After sufficient time has elapsed to allow a significant number of $cS1P_1$ receptors to be expressed and become integrated into the membranes of the cells, the cells are harvested. In the case of adherent cells, the transfected cells are harvested with an enzyme-free dissociation solution to dislodge the cells from the surface of the tissue culture dishes without causing damage to the $cS1P_1$ integrated into the membranes of the cells. The cells are pelleted by low speed centrifugation and suspended in a buffer. Membranes are prepared from the cells and aliquots of the membranes are transferred to buffer containing labeled S1P and analyte to be tested. After incubating for a time sufficient for S1P and/or analyte to bind the $cS1P_1$, unbound labeled S1P and analyte are removed and the amount of labeled S1P is then detected by a method suitable for detecting the label. Non-specific binding can be defined as the amount of label bound to the $cS1P_1$ receptor on the cells in the presence of about 200 nM unlabeled S1P.

In variations of the assay, a plurality of membrane aliquots are mixed with aliquots of the mixture containing different concentrations of the analyte to be tested. Analytes that cause a decrease in the amount of label retained relative to controls comprising the labeled S1P and no analyte are analytes that bind to the $cS1P_1$ receptor. Serial dilutions of the analyte in the presence of a fixed amount of labeled S1P enable the affinity of the analyte for the $cS1P_1$ receptor to be determined. In an alternative embodiment of the above assay, the S1P is unlabeled and the analyte is labeled. In this case, analytes which bind the $cS1P_1$ receptor are determined by detecting the amount of labeled analyte bound in the absence and presence of various concentrations of S1P.

A GTP binding assay is an example of a cell-free method which can be used to not only measure binding of an analyte to the $cS1P_1$ receptor but also to determine whether the analyte can modulate activity of the $cS1P_1$ receptor. Therefore, in a further aspect of a cell-free assay for determining whether an analyte is an agonist or antagonist, a labeled-GTPγS cell-free binding assay method can be used. In this assay, membranes are prepared from transfected cells and aliquots incubated in a mixture with GDP, various concentrations of the analyte, and labeled GTPγS. After incubating for a time sufficient for the labeled GTPγS to bind the G protein, the reaction is terminated and the bound labeled GTPγS is measured by a means suitable for detecting the label. The GTPγS can be labeled by any standard technique known in the art, such as radiolabeling, fluorescence labeling, Europium labeling, or the like. In variations of the assay, a plurality of membrane aliquots are mixed with aliquots of the mixture containing different concentrations of the analyte to be tested. Controls include S1P in the absence of the analyte.

When the method is performed in the absence of S1P, analytes that stimulate labeled GTPγS binding greater than the endogenous level (or non-specific binding level) are agonists while compounds that inhibit the endogenous level of labeled GTPγS are inverse agonists. This is detected as label associated with the membrane. On the other hand, antagonists are detected in a labeled GTPγS binding assay in the presence of a submaximal level of S1P or other known agonist where they reduce the labeled GTPγS binding that is stimulated by S1P. Determination of the amount of binding in the presence of varying concentrations of analyte and analysis of the data by a computer program such as PRISM software (GraphPad) can measure the affinity of analytes for the $cS1P_1$ receptor. Specificity of analytes for the $cS1P_1$ receptor can be determined by measuring the level of labeled GTPγS binding in the presence of the analyte to other G protein coupled receptors (e.g., S1P$_2$, S1P$_3$, S1P$_4$, S1P$_5$, or the like) in similar binding assays using membranes prepared from cells transfected with each respective receptor.

In a further aspect of the method, the analyte is labeled with a label that is different from the label of the GTPγS. For example, the analyte can be labeled with a first fluorescent label which fluoresces at a first wavelength and the GTPγS is labeled with a second fluorescent label which fluoresces at a second wavelength or a radioisotope such as $^{35}$S or europium. In this embodiment, a labeled analyte, which is an agonist, will bind to the cS1P$_1$ receptor on the membrane and will stimulate binding of the labeled GTPγS to the G protein of the membrane. Both labels will be substantially associated with the membrane and detectable. That is association of both labels with the membrane will be greater than the endogenous level or the non-specific binding level. In contrast, a labeled analyte, which is an antagonist, will bind to the cS1P$_1$ receptor on the membrane but will not stimulate binding of the labeled GTPγS to the G protein of the membrane. The label of the analyte will be substantially associated with the membrane and detectable at a level greater than the endogenous level or the non-specific binding level. However, the labeled GTPγS will not be detectable at a level greater than the endogenous level or the non-specific binding level.

In further aspects of the GTPγS-based method, detection of agonist or antagonist activity of an analyte is determined by determining whether in the presence of the analyte the Gα subunit is activated or rendered inactive. Detection of activated or inactivated Gα subunit can be achieved by including in the assay or subsequent to the assay an antibody or peptide which is specific for and binds either the activated or inactivated form of the Gα subunit. Preferably, the antibody or peptide is labeled.

In various embodiments of the above cell-free assay methods, it may be desirable to immobilize the cS1P$_1$ receptor or a target protein of the cS1P$_1$ receptor to facilitate separation of complexed from uncomplexed forms of one or both, as well as to accommodate automation of the assay. Binding of an analyte to cS1P$_1$ receptor, or interaction of the cS1P$_1$ receptor with a target protein in the presence and absence of an analyte, can be accomplished in any vessel suitable for containing the reactants. Examples of such vessels include microtitre plates, test tubes, microarrays, and microcentrifuge tubes.

In one embodiment, a fusion protein can be provided which adds a domain that allows one or both of the proteins to be bound to a matrix. For example, glutathione-S-transferase (GST) fusion proteins or glutathione-S-transferase fusion proteins can be adsorbed onto glutathione SEPHAROSE beads (Sigma Chemical; St. Louis, Mo.) or glutathione derivatized microtitre plates, which are then combined with the analyte or the analyte and either the non-adsorbed target protein or the cS1P$_1$ receptor, and the mixture incubated under conditions conducive to complex formation (for example, at physiological conditions for salt and pH). Following incubation, the beads or microtitre plate wells are washed to remove any unbound components and complex formation is measured. Alternatively, the complexes can be dissociated from the matrix, and the level of binding or activity of the cS1P$_1$ receptor can be determined using standard techniques. Other techniques for immobilizing proteins on matrices can also be used in the screening assays of the invention. For example, either the cS1P$_1$ receptor or its target protein can be immobilized utilizing conjugation of biotin and streptavidin. Biotinylated cS1P$_1$ receptor or target molecules can be prepared from biotin-NHS (N-hydroxy-succinimide) using techniques well known in the art (for example, biotinylation kit, Pierce Chemicals, Rockford, Ill.), and immobilized in the wells of streptavidin coated plates (Pierce Chemical). Alternatively, antibodies reactive with the cS1P$_1$ receptor or target proteins but which do not interfere with binding of the cS1P$_1$ receptor to its target protein can be derivatized to the wells of the plate and unbound target protein or cS1P$_1$ receptor trapped in the wells by antibody conjugation. Methods for detecting such complexes, in addition to those described herein for the GST-immobilized complexes, include immunodetection of complexes using antibodies specific for the cS1P$_1$ receptor or target protein, as well as enzyme-linked assays which rely on detecting an enzymatic activity associated with the cS1P$_1$ receptor or target protein.

The present invention further provides screening assays for monitoring the expression of the cS1P$_1$ receptor. For example, regulators of expression of the cS1P$_1$ receptor can be identified in a method in which a cell is contacted with an analyte and the expression of cS1P$_1$ receptor (protein or mRNA) in the cell is determined. The level of expression of the cS1P$_1$ receptor in the presence of the analyte is compared to the level of expression of the cS1P$_1$ receptor in the absence of the analyte wherein a change in the level of expression indicates that the analyte can regulate expression of the cS1P$_1$ receptor. For example, an increase in cS1P$_1$ receptor levels in the presence of an analyte indicates that the analyte is a stimulator or inducer of cS1P$_1$ receptor expression. Conversely, an analyte that causes a decrease in cS1P$_1$ receptor levels is an inhibitor of cS1P$_1$ receptor expression. The level of cS1P$_1$ receptor in the cells can be determined by methods well known in the art such as RT-PCR (preferably real-time RT-PCR), Northern blotting, or Western blotting. Preferably, the nucleic acid encoding the cS1P$_1$ receptor is operably linked to its native promoter or an S1P$_1$ promoter from a non-*canis* organism.

The method of the present invention can be used for high throughput screening (HTS) of analytes to identify analytes that bind CS1P$_1$ and/or are modulators of cS1P$_1$ receptor activity. Often chemical entities with useful properties are generated by identifying a chemical compound (called a "lead compound") with some desirable property or activity, creating variants of the lead compound, and evaluating the property and activity of those variant compounds. The current trend is to shorten the time scale for all aspects of drug discovery. Because of the ability to test large numbers quickly and efficiently, high throughput screening (HTS) methods are replacing conventional lead compound identification methods.

In one aspect, high throughput screening methods involve providing a library containing a large number of potential cS1P$_1$ modulators (candidate compounds). Such "combinatorial chemical libraries" are then screened in one or more of the assays described herein, to identify those library members particular chemical species or subclasses that display a desired characteristic activity. The compounds thus identified can serve as conventional "lead compounds" or can themselves be used as potential cS1P$_1$ modulators.

Devices for the preparation of combinatorial libraries are commercially available (See, for example, 357 MPS, 390 MPS, Advanced Chem Tech, Louisville, Ky.; Symphony, Rainin, Woburn, Mass.; 433A Applied Biosystems, Foster City, Calif.; 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett- Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (See, for example, ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.).

Any of the assays described herein are amenable to high throughput screening. As described above, the $cS1P_1$ receptor modulators are preferably screened by the methods disclosed herein. High throughput systems for such screening are well known to those of skill in the art. Thus, for example, U.S. Pat. No. 5,559,410 discloses high throughput screening methods for protein binding, while U.S. Pat. Nos. 5,576,220 and 5,541,061 disclose high throughput methods of screening for ligand/antibody binding.

In addition, high throughput screening systems are commercially available (See, for example, Zymark Corp., Hopkinton, Mass.; Air Technical Industries, Mentor, Ohio; Beckman Instruments, Inc. Fullerton, Calif.; Precision Systems, Inc., Natick, Mass.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols. Thus, for example, Zymark Corp. provides technical bulletins describing screening systems for detecting the modulation of gene transcription, ligand binding, and the like.

The following examples are intended to promote a further understanding of the present invention.

EXAMPLE 1

A full length nucleotide sequence encoding the $cS1P_1$ receptor was obtained by RT-PCR and RACE (rapid amplification of cDNA end) PCR methods using dog genomic DNA (Novagen) and cDNA libraries as templates. The cDNA libraries were prepared from dog heart and brain RNA using a SMART RACE cDNA Amplification kit (BD Bioscience). RACE primers were designed from a partial $cS1P_1$ receptor sequence (GenBank database accession number AY011741) and are listed in Table 1 as CM012, CM012-r, CM001-r, and CM004. In the primer sequences shown, M is A or C, R is A or G, Y is C or T, S is C or G, and N is any nucleotide.

For RACE amplification, reagents from the SMART RACE cDNA Amplification Kit were combined with 200 nM each primer (Qiagen) and 2.5 uL of heart or brain cDNA. An Applied Biosystem GeneAmp PCR 9700 instrument was used with the following cycling conditions: 5 cycles at 94° C. for 5 seconds and 72° C. for 3 minutes; 5 cycles at 94° C. for 5 seconds, 70° C. for 10 minutes, and 72° C. for 3 minutes; 25 cycles at 94° C. for 5 seconds and 68° C. for 10 seconds; and, 1 cycle at 72° C. for 3 minutes. RACE amplification products were then used as templates to perform nested RACE reactions using primers CM012, CM012-r, CM001-r, CM004, and CM001 and the same cycling parameters as listed above. RACE products were cloned into the TA cloning vector pCR4-TOPO (Invitrogen) and transformed into TOP10 E. coli cells (Invitrogen). Single colonies were inoculated into LB media with ampicillin and grown overnight at 37° C. DNA was purified from colonies using QIAPREP Turbo Miniprep Kit (QIAGEN). Plasmid DNA was sent for primer extension sequencing (SEQWRIGHT) using gene specific and universal primers. Sequence analysis, based on amino acid homology with the human $S1P_1$ gene, indicated a complete sequence at the 3' end including the stop codon and some 3' untranslated sequence, and an incomplete RACE product at the 5' end that did not include the predicted start codon.

To obtain the full length 5' end of the $cS1P_1$, degenerate primers D5p-1, D5p-2, D5p-3, and D5p-4r were designed upstream of the start codon based on the nucleotide alignment of the full length human, mouse, and rat $S1P_1$ sequences with the partial dog $cS1P_1$ sequence. PCR was performed using dog genomic DNA (Novagen) as template with the degenerate and RACE primers and Platinum Pfx enzyme (Invitrogen). PCR conditions were as follows: 1 cycle at 94° C. for 30 seconds; 5 cycles at 94° C. for 10 seconds and 72° C. for 2 minutes; 5 cycles at 94° C. for 30 seconds and 66° C. for 2 minutes; 25 cycles at 94° C. for 10 seconds, 63° C. for 3 minutes, and 72° C. for 1 minutes; and, 1 cycle at 72° C. for 7 minutes. PCR products were cloned into the TA cloning vector pCR4-TOPO (Invitrogen) and transformed into TOP10 E. coli cells (Invitrogen). Single colonies were inoculated into LB media with ampicillin and grown overnight at 37° C. DNA was purified from colonies using QIAPREP Turbo Miniprep Kit (QIAGEN). Plasmid DNA was sent for primer extension sequencing (SEQWRIGHT).

The full length $cS1P_1$ gene had 1146 bp of nucleotide sequence shown as SEQ ID NO:1. The 382 amino acid protein shown as SEQ ID NO:2 had greater than 90% identity to the human and rat $S1P_1$ receptors.

TABLE 1

| Name | Sequence 5' to 3' | SEQ ID NO: | Tm | % GC | Location (in part seq) |
|---|---|---|---|---|---|
| CM001 | GCAACAGCTTCCGCTCCTTCCTGC | 3 | 70.5 | 62.5 | 316-339 |
| CM001-r | GCAGGAAGGAGCGGAAGCTGTTGC | 4 | 70.5 | 62.5 | 316-339 |
| CM012 | CATCATGGGCTGGAACTGCATCGGCG | 5 | 71.1 | 61.5 | 386-411 |
| CM012-r | CGCCGATGCAGTTCCAGCCCATGATG | 6 | 71.1 | 61.5 | 386-411 |
| CM004-r | TCTTGCGGAAGGTCAGGCGGCGG | 7 | 72.4 | 69.6 | 548-570 |
| CM014-r | CAGGTCAGACAGGGCCAGGTTGC | 8 | 70.6 | 65.2 | 106-129 |

TABLE 1-continued

| Name | Sequence 5' to 3' | SEQ ID NO: | Tm | % GC | Location (in part seq) |
|---|---|---|---|---|---|
| CM015-r | GTACATAGGTCGGTGGAACTTC | 9 | 63.4 | 50.0 | 74-95 |
| CM016-r | GCCAGGTTGCGGATGAAATAGTAC | 10 | 65.4 | 50.0 | 92-114 |
| D5p-1 | GCCCTCTCCAGCCAAGGAAAARCTMC | 11 | 69.6 | 57.7 | upstream ATG |
| D5p-2 | CCTCGCCCTCTAGCGTTYGYCTGGAG | 12 | 72.7 | 65.4 | upstream ATG |
| D5p-3 | CTCRNCCTCGCCCTCTAGCGTT | 13 | 69.0 | 63.6 | upstream ATG |
| D5p-4r | SAACTATGATATCATMGTCCGGC | 14 | 62.6 | 45.6 | upstream ATG |
| D5p-5r | CRGTGGTGTTCATYCTCATCTGCTGC | 15 | 68.0 | 53.8 | -3-23 |
| DE1-HF | cAAGCTTatggggtccaccagcgtcc | 16 | 71 | 61.5 | — |
| D5r | CTCCCCCATGGGTCGGCGGCTTTCAGTTCTCGAG | 17 | 76.7 | | |

EXAMPLE 2

To obtain a clone encoding the entire cS1P$_1$ gene, dog genomic DNA was PCR amplified using primers DEL-HF and D5r (Table 1) designed from the sequencing information. PCR reactions with Pfu Turbo (Stratagene) polymerase were conducted using the following cycling conditions: 1 cycle at 94° C. for 30 seconds; 5 cycles at 94° C. for 30 seconds and 72° C. for 2 minutes; 5 cycles at 94° C. for 30 seconds and 70° C. for 2 minutes; 25 cycles at 94° C. for 30 seconds, 68° C. for 1 minutes, and 72° C. for 2 minutes; and, 1 cycle at 72° C. for 7 minutes. The PCR product was cloned into the pCR2.1-TOPO cloning vector and transformed into TOP10 E. coli cells (Invitrogen). The clone chosen for expression studies had one base pair change in the nucleotide sequence compared to the sequence shown in SEQ ID NO:1; however, the sequence encoded the same amino acid sequence as shown in SEQ ID NO:2. The plasmid DNA was cut with EcoRI and fragment containing cS1P$_1$ was ligated into pcDNA3.1 (+) zeocin. The sequence was confirmed and DNA was prepared using an endotoxin-free maxi-prep kit (QIAGEN).

Chinese Hamster Ovary (CHO) cells (about $1.6 \times 10^6$) were transfected with 6 µg of DNA and 8 µL of lipofectamine using a modified protocol from Life Technologies. After a 5 hour recovery, zeocin selection was added to the cells, which were split to pools the next day. Cells were subsequently split several times to enrich the population of zeocin resistant cells. Pools were screened for gene expression using a whole cell S1P binding assay. Membranes prepared from pools were screened for expression using the S1P binding assay and the GTPγS binding assay.

EXAMPLE 3

The transfected CHO cells from Example 2 expressing the cS1P$_1$ receptor were evaluated for the ability of the cS1P$_1$ receptor expressed in the cells to properly integrate into the cell membrane and bind S1P.

Transfected CHO cells from Example 2 were harvested with enzyme-free dissociation solution (Specialty Media, Lavallette, N.J.). The cells were washed once in cold PBS and suspended in S1P binding buffer (50 mM HEPES-Na, pH 7.5, 5 mM MgCl$_2$, 1 mM CaCl$_2$, 0.5% FAF-BSA). $^{33}$P-S1P was synthesized enzymatically from γ$^{33}$P-ATP and sphingosine using a crude extract with sphingosine kinase activity in a reaction mix containing 50 mM KH$_2$PO$_4$, 1 mM mercaptoethanol, 1 mM Na$_3$VO$_4$, 25 mM KF, 2 mM semicarbazide, 1 mM Na$_2$EDTA, 5 mM MgCl$_2$, 50 mM sphingosine, 0.1% TritonX-114, and 1 mCi γ$^{33}$P-ATP (NEN; specific activity 2000 Ci/mmol). Reaction products were extracted with butanol and $^{33}$P-S1P was purified by HPLC.

$^{33}$P-S1P (0.1 uCi/ml) was sonicated with 0.2 nM S1P dissolved in binding buffer; 100 µL of the mixture was added to 100 µL cells ($1 \times 10^5$). Binding was performed for 60 minutes at room temperature. Cells were then collected onto GF/B filter plates with a Packard Filtermate Universal Harvester. After drying the filter plates for 30 minutes, 50 µL of MICROSCINT 20 was added to each well and binding was measured with a Packard Top Count. Non-specific binding was defined as the amount of radioactivity remaining in the presence of 200 nM cold S1P.

The results shown in FIG. 3 show that transfected cells ectopically expressing the cS1P$_1$ receptor were able to bind the labeled S1P. As shown by the results in FIG. 3, the EC$_{50}$ was about 0.37 nM. This indicates that the cS1P$_1$ receptor expressed in the CHO cells was properly integrated into the cell membrane and was able to bind the S1P.

Alternatively, ligand binding can be measured with membranes prepared from cells expressing cS1P$_1$. Membranes are prepared from transfected cells by homogenization in ice cold 20 mM HEPES pH 7.4, 10 mM EDTA using a Kinematica polytron (setting 5, for 10 seconds). Homogenates are centrifuged at 48,000×g for 15 minutes at 4° C. and the pellet suspended in 20 mM HEPES pH 7.4, 0.1 mM EDTA. Following a second centrifugation, the final pellet is suspended in 20 mM HEPES pH 7.4, 100 mM NaCl, 10 mM MgCl$_2$. The $^{33}$P-S1P mixture is mixed with membranes diluted in binding buffer to a protein concentration of 5 to 25 µg/ml, and binding is performed as described for cells.

EXAMPLE 4

A cell-free assay was used to show that the cS1P$_1$ receptor ectopically expressed in CHO cells was able to functionally couple GTP to Gα.

Functional coupling of the cS1P$_1$ receptor to G proteins was measured in a $^{35}$S-GTPγS binding assay. Membranes were prepared from transfected cells by homogenization in ice cold 20 mM HEPES pH 7.4, 10 mM EDTA using a Kinematica polytron (setting 5, for 10 seconds). Homogenates were centrifuged at 48,000×g for 15 minutes at 4° C. and the pellet suspended in 20 mM HEPES pH 7.4, 0.1 mM EDTA. Following a second centrifugation, the final pellet was suspended in 20 mM HEPES pH 7.4, 100 mM NaCl, 10 mM MgCl$_2$. Membranes were incubated in 200 µL with 5 µM GDP, various concentrations of S1P (sonicated in 1% BSA), and 100 pM $^{35}$S-GTPγS (NEN; specific activity 1250 Ci/mmol) in 96 well microtiter dishes. Binding was performed for one hour at room temperature, and terminated by harvesting the membranes onto GF/B filter plates with a Packard Filtermate Universal Harvester. After drying the filter plates for 30 min, 40 µL of MICROSCINT 20 was added to each well and binding was measured on a Packard Top Count scintillation counter.

Figure 4:
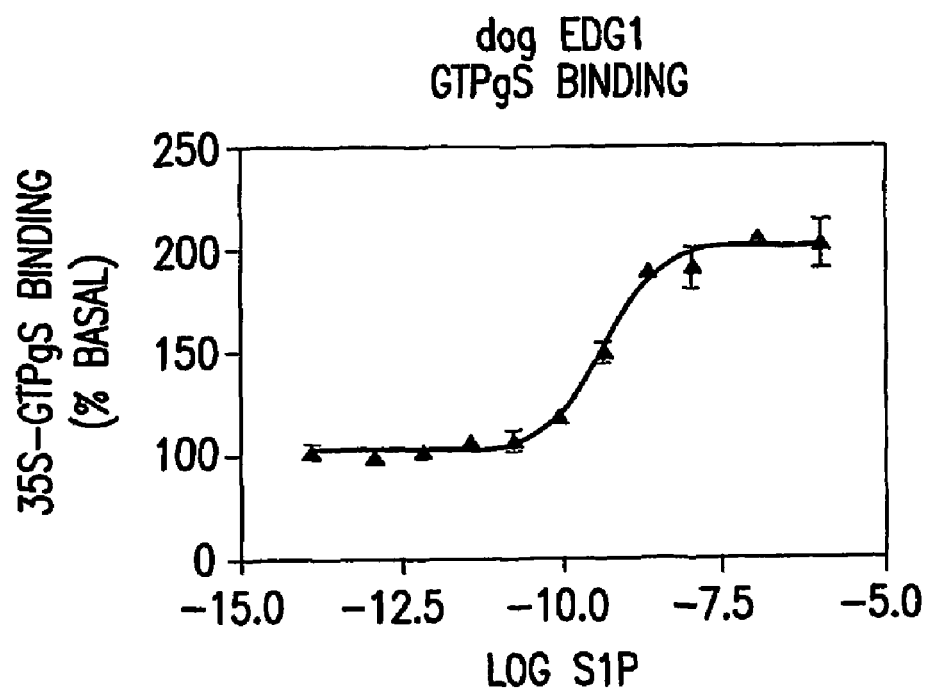
FIG. 4 shows the results of a GTPγS binding assay using the cS1P$_1$ receptor.

The results shown in FIG. 4 show that the cS1P$_1$ receptor in the presence of its ligand was capable of coupling GTP to Gα. As shown by the results in FIG. 4, the EC$_{50}$ was about 0.42 nM. This result indicates that the ectopically expressed the cS1P$_1$ receptor was functional.

EXAMPLE 5

A cell-based competition assay for detecting analytes that are competitor of S1P binding to cS1P$_1$ receptor and determining their affinity for the cS1P$_1$ receptor can be preformed as follows.

Transfected CHO cells from Example 2 are harvested with enzyme-free dissociation solution (Specialty Media, Lavallette, N.J.). The cells were washed once in cold PBS and suspended in S1P binding buffer (50 mM HEPES-Na, pH 7.5, 5 mM MgCl$_2$, 1 mM CaCl$_2$, 0.5% FAF-BSA). $^{33}$P-SIP is synthesized enzymatically from γ$^{33}$P-ATP and sphingosine using a crude extract with sphingosine kinase activity in a reaction mix containing 50 mM KH$_2$PO$_4$, 1 mM mercaptoethanol, 1 mM Na$_3$VO$_4$, 25 mM KF, 2 mM semicarbazide, 1 mM Na$_2$EDTA, 5 mM MgCl$_2$, 50 mM sphingosine, 0.1% TritonX-114, and 1 mCi γ$^{33}$P-ATP (NEN; specific activity 2000 Ci/mmol). Reaction products are extracted with butanol and $^{33}$P-SIP is purified by HPLC.

$^{33}$P-S1P (0.1 uCi/ml) is sonicated with 0.2 nM sphingosine-1-phosphate and analyte dissolved in binding buffer and 100 µl of the mixture is added to 100 µL cells (1×10$^5$) or membranes prepared from cells. Binding is performed for 60 minutes at room temperature. Cells are then collected onto GF/B filter plates with a Packard Filtermate Universal Harvester. After drying the filter plates for 30 minutes, 50 µL of MICROSCINT 20 is added to each well and binding is measured with a Packard Top Count. Non-specific binding is defined as the amount of radioactivity remaining in the presence of 200 nM cold S1P. Controls consist of the above assay performed in the absence of the analyte and the above assay performed in the absence of the $^{33}$-P-S1P.

Determination of the amount of binding in the presence of varying concentrations of analyte and analysis of the data by PRISM software (GraphPad Software, Inc. San Diego, Calif.) is used to measure the affinity of analytes for the cS1P$_1$ receptor. Specificity of analytes for the cS1P$_1$ receptor is determined by measuring the level of $^{33}$P-S1P binding in the presence of the analyte to related S1P receptors (S1P$_1$, S1P$_3$, S1P$_4$, S1P$_5$, canis or non-canis) in similar binding assays using membranes prepared from cells transfected with each respective receptor.

EXAMPLE 6

A cell-free competition binding assay for detecting analytes that are competitors of S1P binding to the cS1P$_1$ receptor and determining the analytes' affinity for the cS1P$_1$ receptor is described.

Transfected CHO cells from Example 2 are harvested with enzyme-free dissociation solution (Specialty Media, Lavallette, N.J.). $^{33}$P-SIP is synthesized enzymatically from γ$^{33}$P-ATP and sphingosine using a crude extract with sphingosine kinase activity in a reaction mix containing 50 mM KH$_2$PO$_4$, 1 mM mercaptoethanol, 1 mM Na$_3$VO$_4$, 25 mM KF, 2 mM semicarbazide, 1 mM Na$_2$EDTA, 5 mM MgCl$_2$, 50 mM sphingosine, 0.1% TritonX-114, and 1 mCi γ$^{33}$P-ATP (NEN; specific activity 2000 Ci/mmol). Reaction products are extracted with butanol and $^{33}$P-SIP is purified by HPLC.

Membranes are prepared from transfected by homogenization in ice cold 20 mM HEPES pH 7.4, 10 mM EDTA using a Kinematica polytron (setting 5, for 10 seconds). Homogenates are centrifuged at 48,000×g for 15 minutes at 4° C. and the pellet suspended in 20 mM HEPES pH 7.4, 0.1 mM EDTA. Following a second centrifugation, the final pellet is suspended in 20 mM HEPES pH 7.4, 100 mM NaCl, 10 mM MgCl$_2$. Membranes are incubated in 200 µL of $^{33}$P-S1P (0.1 uCi/ml) sonicated with 0.2 nM sphingosine-1-phosphate and analyte dissolved in binding buffer. Binding is performed for 60 minutes at room temperature and terminated by harvesting the membranes onto GF/B filter plates with a Packard Filtermate Universal Harvester. After drying the filter plates for 30 min, 40 µL of MICROSCIT 20 is added to each well and binding is measured on a Packard Top Count scintillation counter. Controls consist of the above assay performed in the absence of the analyte and the above assay performed in the absence of the 33-P-S1P.

Determination of the amount of binding in the presence of varying concentrations of analyte and analysis of the data by PRISM software (GraphPad Software, Inc. San Diego, Calif.) is used to measure the affinity of analytes for the cS1P$_1$ receptor. Specificity of analytes for the cS1P$_1$ receptor is determined by measuring the level of $^{33}$P-S1P binding in the presence of the analyte to related S1P receptors (S1P$_2$, S1P$_3$, S1P$_4$, S1P$_5$, canis or non-canis) in similar binding assays using membranes prepared from cells transfected with each respective receptor.

EXAMPLE 7

A cell-free assay for determining whether an analyte is an agonist or an antagonist and its affinity for the cS1P$_1$ receptor can use the $^{35}$S-GTPγS binding assay of Example 4 as follows.

Membranes are prepared from transfected cells (made as in Example 2) by homogenization in ice cold 20 mM HEPES pH 7.4, 10 mM EDTA using a Kinematica polytron (setting 5, for 10 seconds). Homogenates are centrifuged at 48,000×g for 15 minutes at 4° C. and the pellet suspended in 20 mM HEPES pH 7.4, 0.1 mM EDTA. Following a second centrifugation, the final pellet is suspended in 20 mM HEPES pH 7.4, 100 mM NaCl, 10 mM $MgCl_2$. Membranes are incubated in 200 µL with 5 µM GDP, various concentrations of analyte in DMSO, methanol, or other solvent (preferably, sonicated in 1% BSA), and 100 pM $^{35}$S-GTPγS (NEN; specific activity 1250 Ci/mmol) in 96 well microtiter dishes. Binding is performed for one hour at room temperature and terminated by harvesting the membranes onto GF/B filter plates with a Packard Filtermate Universal Harvester. After drying the filter plates for 30 min, 40 µL of MICROSCINT 20 is added to each well and binding is measured on a Packard Top Count scintillation counter. Controls consist of performing the above assay in the absence of S1P to determine the endogenous level of GTPγS binding.

Determination of the amount of binding in the presence of varying concentrations of compound and analysis of the data by PRISM software (GraphPad) is used to measure the affinity of compounds for the $cS1P_1$ receptor. Specificity of compounds for the $cS1P_1$ receptor is determined by measuring the level of $^{35}$S-GTPγS binding in the presence of the analyte to other G protein coupled receptors in similar binding assays using membranes prepared from cells transfected with each respective receptor. When the method is performed in the absence of S1P, analytes that stimulate labeled GTPγS binding above the endogenous level are agonists while compounds that inhibit the endogenous level of labeled GTPγS are considered inverse agonists. On the other hand, antagonists are detected in a labeled GTPγS binding assay in the presence of a submaximal level of S1P or other known agonist where they reduce the labeled GTPγS binding that is stimulated by the agonist.

EXAMPLE 8

This example describes a method for making polyclonal antibodies specific for the $cS1P_1$ receptor or particular peptide fragments or epitope thereof.

The $cS1P_1$ receptor is produced in *E. coli* transformed with the vector of Example 2. Antibodies are generated in New Zealand white rabbits over a 10-week period. The $cS1P_1$ receptor or peptide fragment or epitope thereof is emulsified by mixing with an equal volume of Freund's complete adjuvant and injected into three subcutaneous dorsal sites for a total of about 0.1 mg $S1P_1$ receptor per immunization. A booster containing about 0.1 mg $cS1P_1$ receptor emulsified in an equal volume of Freund's incomplete adjuvant is administered subcutaneously two weeks later. Animals are bled from the articular artery. The blood is allowed to clot and the serum collected by centrifugation. The serum is stored at −20° C.

For purification, the $cS1P_1$ receptor is immobilized on an activated support. Antisera is passed through the sera column and then washed. Specific antibodies are eluted via a pH gradient, collected, and stored in a borate buffer (0.125M total borate) at −0.25 mg/mL. The anti-$cS1P_1$ receptor antibody titers are determined using ELISA methodology with free $cS1P_1$ receptor bound in solid phase (1 pg/well). Detection is obtained using biotinylated anti-rabbit IgG, HRP-SA conjugate, and ABTS.

EXAMPLE 9

This example describes a method for making monoclonal antibodies specific for the $cS1P_1$ receptor.

BALB/c mice are immunized with an initial injection of about 1 µg of purified $cS1P_1$ receptor per mouse mixed 1:1 with Freund's complete adjuvant. After two weeks, a booster injection of about 1 µg of the antigen is injected into each mouse intravenously without adjuvant. Three days after the booster injection serum from each of the mice is checked for antibodies specific for the $S1P_1$ receptor.

The spleens are removed from mice positive for antibodies specific for the $cS1P_1$ receptor and washed three times with serum-free DMEM and placed in a sterile Petri dish containing about 20 mL of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 mL 0.17 M ammonium chloride and placed on ice for several minutes. Then 5 mL of 20% bovine fetal serum is added and the cells pelleted by low-speed centrifugation. The cells are then resuspended in 10 mL DMEM and mixed with mid-log phase myeloma cells in serum-free DMEM to give a ratio of 3:1. The cell mixture is pelleted by low-speed centrifugation, the supernatant fraction removed, and the pellet allowed to stand for 5 minutes. Next, over a period of 1 minute, 1 mL of 50% polyethylene glycol (PEG) in 0.01 M HEPES, pH 8.1, at 37° C. is added. After 1 minute incubation at 37° C., 1 mL of DMEM is added for a period of another 1 minute, then a third addition of DMEM is added for a further period of 1 minute. Finally, 10 mL of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 µM aminopterin, and 10% hybridoma cloning factor (HAT medium). The cells are then plated into 96-well plates.

After 3, 5, and 7 days, half the medium in the plates is removed and replaced with fresh HAT medium. After 11 days, the hybridoma cell supernatant is screened by an ELISA assay. In this assay, 96-well plates are coated with the $cS1P_1$ receptor. One hundred µL of supernatant from each well is added to a corresponding well on a screening plate and incubated for 1 hour at room temperature. After incubation, each well is washed three times with water and 100 µL of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 µL of 1 M HCl is added to stop the reaction and the absorbance of the wells is measured at 490 nm. Cultures that have an absorbance greater than the control wells are removed to two $cm^2$ culture dishes, with the addition of normal mouse spleen cells in HAT medium. After a further three days, the cultures are re-screened as above and those that are positive are cloned by limiting dilution. The cells in each two cm2 culture dish are counted and the cell concentration adjusted to $1\times10^5$ cells per mL. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 $cm^2$ cultures and provided with normal mouse spleen cells. This cloning procedure is repeated until stable antibody producing hybridomas are obtained. The stable hybridomas are progressively expanded to larger culture dishes to provide stocks of the cells.

Production of ascites fluid is performed by injecting intraperitoneally 0.5 mL of pristane into female mice to prime the mice for ascites production. After 10 to 60 days, 4.5×106 cells are injected intraperitoneally into each mouse and ascites fluid is harvested between 7 and 14 days later.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An isolated nucleic acid molecule comprising a nucleotide sequence encoding a *Canis* sphingosine-1-phosphate isoform 1 ($cS1P_1$) receptor which comprises the amino acid sequence set forth in SEQ ID NO:2.

2. An isolated nucleic acid molecule comprising the nucleotide sequence set forth in SEQ ID NO:1.

3. An isolated protein comprising the amino acid sequence Of SEQ ID NO:2.

4. A method for identifying an analyte that modulates activity of a *Canis* sphingosine-1-phosphate receptor isoform 1 ($cS1P_1$) receptor, which comprises:
   (a) providing a recombinant cell comprising an isolated nucleic acid molecule which encodes a $cS1P_1$ receptor comprising the amino acid sequence set forth in SEQ ID NO: 2;
   (b) incubating the recombinant cell in a medium with the analyte such that the cell expresses the $cS1P_1$ receptor; and
   (c) determining the activity of the $cS1P_1$ receptor wherein a change in the activity of the $cS1P_1$ receptor indicates the analyte modulates activity of the $cS1P_1$ receptor.

5. The method of claim 4 wherein the activity of the $cS1P_1$ is determined by measuring a change in the intracellular concentration of $Ca^{2+}$ in the presence of the analyte.

6. The method of claim 4 wherein the activity of the $cS1P_1$ is determined by measuring a change in the intracellular concentration of a metabolite selected from the group consisting of inositol triphosphate ($IP_3$) and diacylglycerol (DAG) in the presence of the analyte.

7. The method of claim 4 wherein the activity of the $cS1P_1$ is determined by measuring a change in the activity of phospholipase C beta ($PLC_\beta$) or protein kinase C (PKC) in the presence of the analyte.

8. The method of claim 4 wherein the activity of the $cS1P_1$ is determined by measuring a change in the synthesis of cyclic AMP (cAMP) in the presence of the analyte.

9. The method of claim 4 wherein the isolated nucleic acid molecule which encodes the $cS1P_1$ receptor comprises the nucleotide sequence set forth in SEQ ID NO:1.

* * * * *